United States Patent
Mourich et al.

(10) Patent No.: US 9,487,786 B2
(45) Date of Patent: *Nov. 8, 2016

(54) IMMUNOSUPPRESSION COMPOUND AND TREATMENT METHOD

(71) Applicant: Sarepta Therapeutics, Inc., Corvallis, OR (US)

(72) Inventors: Dan V. Mourich, Albany, OR (US); Patrick L. Iversen, Corvallis, OR (US); Dwight D. Weller, Corvallis, OR (US)

(73) Assignee: SAREPTA THERAPEUTICS, INC., Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/581,485

(22) Filed: Dec. 23, 2014

(65) Prior Publication Data

US 2015/0184165 A1 Jul. 2, 2015

Related U.S. Application Data

(63) Continuation of application No. 13/940,098, filed on Jul. 11, 2013, now Pat. No. 8,933,216, which is a continuation of application No. 12/267,437, filed on Nov. 7, 2008, now Pat. No. 8,501,704, which is a (Continued)

(51) Int. Cl.
*C12N 15/11* (2006.01)
*A61K 48/00* (2006.01)
(Continued)

(52) U.S. Cl.
CPC ......... *C12N 15/1138* (2013.01); *C12N 15/113* (2013.01); *C12N 2310/11* (2013.01); *C12N 2310/314* (2013.01); *C12N 2310/3233* (2013.01); *C12N 2310/3513* (2013.01)

(58) Field of Classification Search
USPC .......................................... 514/44; 536/24.5
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |

(Continued)

FOREIGN PATENT DOCUMENTS

| | | |
|---|---|---|
| WO | WO 93/00431 A1 | 1/1993 |
| WO | 97/40854 A2 | 11/1997 |

(Continued)

OTHER PUBLICATIONS

Agrawal et al., "Antisense Therapeutics: Is it as Simple as Complementary Base Recognition?", *Molecular Medicine Today* 6(2): 72-81, Feb. 2000.

(Continued)

*Primary Examiner* — Terra C Gibbs
(74) *Attorney, Agent, or Firm* — Seed IP Law Group LLP

(57) ABSTRACT

A method and compound for suppressing an immune response in a mammalian subject, for the treatment or prevention of an autoimmune condition or transplantation rejection are disclosed. The compound is an antisense oligonucleotide analog compound having a targeting sequence complementary to a preprocessed CTLA-4 mRNA region identified by SEQ ID NO: 22 in SEQ ID NO: 1, spanning the splice junction between intron 1 and exon 2 of the preprocessed mRNA of the subject. The compound is effective, when administered to a subject, to form within host cells, a heteroduplex structure (i) composed of the preprocessed CTLA-4 mRNA and the oligonucleotide compound, (ii) characterized by a Tm of dissociation of at least 45° C., and (iii) resulting in an increased ratio of processed mRNA encoding ligand-independent CTLA-4 to processed mRNA encoding full-length CTLA-4.

21 Claims, 15 Drawing Sheets

Related U.S. Application Data continuation-in-part of application No. 11/595,161, filed on Nov. 8, 2006, now abandoned.

(60) Provisional application No. 60/799,976, filed on May 11, 2006, provisional application No. 60/735,000, filed on Nov. 8, 2005.

(51) Int. Cl.
*C07H 21/02* (2006.01)
*C07H 21/04* (2006.01)
*C12N 15/113* (2010.01)

(56) References Cited

U.S. PATENT DOCUMENTS

| | | |
|---|---|---|
| 5,166,315 A | 11/1992 | Summerton et al. |
| 5,185,444 A | 2/1993 | Summerton et al. |
| 5,217,866 A | 6/1993 | Summerton et al. |
| 5,434,131 A | 7/1995 | Linsley et al. |
| 5,495,006 A | 2/1996 | Climie et al. |
| 5,506,337 A | 4/1996 | Summerton et al. |
| 5,521,063 A | 5/1996 | Summerton et al. |
| 5,576,302 A | 11/1996 | Cook et al. |
| 5,580,767 A | 12/1996 | Cowsert et al. |
| 5,698,685 A | 12/1997 | Summerton et al. |
| 5,698,695 A | 12/1997 | Appleton et al. |
| 5,702,891 A | 12/1997 | Kolberg et al. |
| 5,734,039 A | 3/1998 | Calabretta et al. |
| 5,738,985 A | 4/1998 | Miles et al. |
| 5,892,023 A | 4/1999 | Pirotzky et al. |
| 5,955,318 A | 9/1999 | Simons et al. |
| 5,989,904 A | 11/1999 | Das et al. |
| 6,060,456 A | 5/2000 | Arnold, Jr. et al. |
| 6,133,246 A | 10/2000 | McKay et al. |
| 6,174,868 B1 | 1/2001 | Anderson et al. |
| 6,214,555 B1 | 4/2001 | Leushner et al. |
| 6,228,579 B1 | 5/2001 | Zyskind et al. |
| 6,239,265 B1 | 5/2001 | Cook |
| 6,258,570 B1 | 7/2001 | Glustein et al. |
| 6,306,993 B1 | 10/2001 | Rothbard et al. |
| 6,365,351 B1 | 4/2002 | Iversen |
| 6,365,577 B1 | 4/2002 | Iversen |
| 6,495,663 B1 | 12/2002 | Rothbard et al. |
| 6,669,951 B2 | 12/2003 | Rothbard et al. |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 6,881,825 B1 | 4/2005 | Robbins et al. |
| 7,049,431 B2 | 5/2006 | Iversen |
| 7,094,765 B1 | 8/2006 | Iversen et al. |
| 7,115,374 B2 | 10/2006 | Linnen |
| 7,358,068 B2 | 4/2008 | Vaillant et al. |
| 7,468,418 B2 | 12/2008 | Iversen et al. |
| 7,615,629 B2 | 11/2009 | Arar |
| 8,084,433 B2 | 12/2011 | Iversen et al. |
| 8,129,352 B2 | 3/2012 | Iversen et al. |
| 8,329,668 B2 | 12/2012 | Stein et al. |
| 8,501,704 B2 | 8/2013 | Mourich et al. |
| 8,524,676 B2 | 9/2013 | Stein et al. |
| 2003/0224353 A1 | 12/2003 | Stein et al. |
| 2004/0072239 A1 | 4/2004 | Renaud et al. |
| 2007/0265214 A1 | 11/2007 | Stein et al. |

FOREIGN PATENT DOCUMENTS

| | | |
|---|---|---|
| WO | WO 01/49775 A1 | 7/2001 |
| WO | WO 01/81916 A2 | 11/2001 |
| WO | WO 01/90122 A2 | 11/2001 |
| WO | WO 02/074989 A2 | 9/2002 |
| WO | WO 02/098456 A2 | 12/2002 |
| WO | WO 03/088991 A1 | 10/2003 |
| WO | WO 2004/081021 A2 | 9/2004 |
| WO | WO 2005/014612 A1 | 2/2005 |
| WO | WO 2007/056466 A2 | 5/2007 |
| WO | WO 2008/036127 A2 | 3/2008 |

OTHER PUBLICATIONS

Agrawal et al., "Oligodeoxynucleoside phosphoramidates and phosphorothioates as inhibitors of human immunodeficiency virus," *Proc. Natl. Acad. Sci. USA* 85:7079-7083, 1988.

Agrawal et al., "Site-specific excision from RNA by RNase H and mixed-phosphate-backbone oligodeoxynucleotides," *Proc Natl Acad Sci USA* 87(4): 1401-1405, 1990.

Anderson et al., "Distribution of equilibrative, nitrobenzylthioinosine-sensitive nucleoside transporters (ENT1) in brain," *Journal of Neurochemistry* 73(2): 867-873, 1999.

Anderson et al., "Inhibition of human cytomegalovirus immediate-early gene expression by an antisense oligonucleotide complementary to immediate-early RNA," *Antimicrobial Agents and Chemotherapy* 40(9): 2004-2011, 1996.

Bonham et al., "An assessment of the antisense properties of RNase H-competent and steric-blocking oligomers," *Nucleic Acids Res* 23(7): 1197-1203, 1995.

Bonham et al., "Marked Prolongation of Cardiac Allograft Survival by Dendritic Cells Genetically Engineered with $NF_K$-B Oligodeoxyribonucleotide Decoys and Adenoviral Vectors Encoding CTLA4-Ig," *The Journal of Immunology* 169:3382-3391, 2002.

Boudvillain et al., "Transplatin-modified oligo(2'-O-methyl ribonucleotide)s: a new tool for selective modulation of gene expression," *Biochemistry* 36(10): 2925-2931, 1997.

Branch, "A good antisense molecule is hard to find," *Trends in Biochem Sci* 23: 45-50, 1998.

Braasch et al., "Novel antisense and peptide nucleic acid strategies for controlling gene expression," *Biochemistry* 41: 4503-4510, 2002.

Ding et al., "An oligodeoxyribonucleotide N3'—P5' phosphoramidate duplex forms an A-type helix in solution," *Nucleic Acids Res* 24(2): 354-360, 1996.

Gee et al., "Assessment of high-affinity hybridization, RNase H cleavage, and covalent linkage in translation arrest by antisense oligonucleotides," *Antisense Nucleic Acid Drug Dev* 8(2): 103-111, 1998.

Geller et al., "Antisense Antibacterial Method and Compound," Office Action mailed Sep. 29, 2010, U.S. Appl. No. 11/173,847, 25 pages.

Gewirtz et al., "Facilitating oligonucleotide delivery: helping antisense deliver on its promise," *Proc Natl Acad Sci USA* 93: 3161-3163, 1996.

Hudziak et al., "Antiproliferative effects of steric blocking phosphorodiamidate morpholino antisense agents directed against c-myc,"*Antisense Nucleic Acid Drug Dev* 10: 163-176, 2000.

Hudziak et al., "Resistance of morpholino phosphorodiamidate oligomers to enzymatic degradation," *Antisense Nucleic Acid Drug Dev* 6: 267-272, 1996.

Iversen et al., "Splice-Region Antisense Composition and Method," Office Action mailed on Apr. 23, 2010, U.S. Appl. No. 11/433,214, 17 pages.

Iversen et al., "Antisense Antiviral Compound and Method for Treating ssRNA Viral Infection," Office Action mailed Oct. 19, 2010, U.S. Appl. No. 11/432,031, 25 pages.

Jen et al., "Suppression of gene expression by targeted disruption of messenger RNA: available options and current strategies," *Stem Cells* 18: 307-319, 2000.

Leach et al, "Enhancement of antitumor immunity by CTLA-4 blockade," *Science* 271: 1734-1736, 1996.

Loke et al., "Characterization of oligonucleotide transport into living cells," *Proc Natl Acad Sci* 86(10): 3474-3478, 1989.

Miura et al., "T Cell Activation and Regulation in Graft-Versus-Host Disease: Integral Role of CD28, CTLA4 and GITR Splice Variants," *Blood (Ash Annual Meeting Abstracts)* 104: Abstract 3054, 2004.

Moulton et al., "HIV Tat peptide enhances cellular delivery of antisense morpholino oligomers," *Antisense Nucleic Acid Drug Dev* 13: 31-43, 2003.

(56) References Cited

OTHER PUBLICATIONS

Moulton and Moulton, "Peptide-assisted delivery of steric-blocking antisense oligomers," *Curr Opin Mol Ther* 5(2): 123-132, 2003.

Moulton et al., "Cellular uptake of antisense morpholino oligomers conjugated to arginine-rich peptides," *Bioconjug Chem* 15(2): 290-299, 2004.

Mourich et al., "Ligand Independent Form of CTLA-4 Induced by Antisense Exon Skipping Alters T-Cell Activity and Inhibits Autoimmune Diabetes in Nod Mice," *Clinical Immunology* 119(Supp): S39, 2006.

Nelson et al., "Arginine-rich peptide conjugation to morpholino oligomers: effects on antisense activity and specificity," *Bioconjugate Chem* 16(4): 959-966, Jul.-Aug. 2005.

Nielsen, "Systemic delivery: the last hurdle," *Gene Therapy* 12: 956-957, 2005.

Pari et al., "Potent antiviral activity of an antisense oligonucleotide complementary to the intron-exon boundary of human cytomegalovirus genes UL36 and UL37," *Antimicrobial Agents and Chemotherapy* 39(5): 1157-1161, 1995.

Stein et al., "A specificity comparison of four antisense types: morpholino, 2'-O-methyl RNA, DNA, and phosphorothioate DNA," *Antisense & Nucleic Acid Drug Development* 7(3): 151-157, 1997.

Stein et al., "Antisense Antiviral Agent and Method for Treating ssRNA Viral Infection," Office Action mailed Feb. 17, 2010, U.S. Appl. No. 11/431,968, 19 pages.

Summerton, "Morpholino antisense oligomers: the case for an RNase H-independent structural type," *Biochim Biophys Acta* 1489(1): 141-158, Dec. 10, 1999.

Summerton et al., "Morpholio and phosphorothioate antisense oligomers compared in cell-free and in-cell systems," *Antisense & Nucleic Acid Drug Development* 7: 63-70, 1997.

Summerton and Weller, "Morpholino antisense oligomers: design, preparation, and properties," *Antisense Nucleic Acid Drug Dev* 7(3): 187-195, 1997.

Tamm et al., "Antisense therapy in oncology: new hope for an old idea?", *The Lancet* 358: 489-497, 2001.

Toulme et al., "Targeting RNA structures by antisense oligonucleotides," *Biochimie* 78(7): 663-673, 1996.

Vijayakrishnan et al., "An autoimmune disease-associated CTLA-4 splice variant lacking the B7 binding domain signals negatively in T cells," *Immunity* 20(5): 563-575, 2004.

Weller et al., "Oligonucleotide Analogs Having Cationic Intersubunit Linkages," Office Action mailed Aug. 18, 2010, U.S. Appl. No. 11/801,885, 6 pages.

Weller et al., "Oligonucleotide Analogs Having Cationic Intersubunit Linkages," Advisory Action mailed Oct. 28, 2010, U.S. Appl. No. 11/801,885, 6 pages.

Wender et al., "The design, synthesis, and evaluation of molecules that enable or enhance cellular uptake: peptoid molecular transporters," *Proc Natl Acad Sci* 97(24): 13003-13008, 2000.

Wilton et al., "RNA Splicing Manipulation: Strategies to Modify Gene Expression for a Variety of Therapeutic Outcomes," *Current Gene Therapy* 5:467-483, 2005.

Yakubov et al., "Mechanism of oligonucleotide uptake by cells: involvement of specific receptors?", *Proc Natl Acad Sci USA* 86(17): 6454-6458, 1989.

European Search Report for Application No. EP 06 84 4293, mailed Aug. 11, 2010, 9 pages.

International Search Report, mailed Jan. 27, 2010, for PCT/US2009/063649, 4 pages.

Written Opinion, mailed Jan. 27, 2010, for PCT/US2009/063649, 5 pages.

1) ΦX-Hae III
2) Blank
3) Control
4) SD3
5) SA3
6) Control
7) SD2
8) SA2
9) SD1
10) AUG 1) ΦX Hae III
2) Negative control
3) Untreated
4) SA3 1µM
5) SA3 0.65 µM
6) SA3 0.5 µM
7) SA2 0.75 µM
8) SA2 0.5 µM
9) Phi-X Hae III
10) NOD Control
11) SD2 1.0 µM
12) SD2 0.65 µM
13) SD2 0.5 µM
14) SD3 1.0 µM
15) SD3 0.65 µM
16) Negative control
17) SD3 0.5 µM

Fig. 5

Mouse

```
         3              4 (SEQ ID 23)   5 (SeqID 11)    6            7              8
◀━━━━━  ◀━━━━━━━━━━━   ◀━━━━━━━━━━━━━━━━━━━━━━━━━━   ━━━━━━━━▶  ◀━━━━━━━   ◀━━━━━━━━
GATCATGAGCCCACTAAGTGCCTTTGGACTTTCCATGTCAG/CCATACAGGTGACCCAACCTCAGTGGTGTTGGCTAGCAGCCATGGTGTGCGCCGCTTG
```

Figure 12A

Human

```
                                   SeqID 5
          SeqID 7       SeqID 6    ◀━━━━━━━    SeqID 4
       ◀━━━━━━━━━━  ◀━━━━━━━━━━━            ◀━━━━━━━━━━
GCAGCGAGTTCACTCAGTTCCGTTTGGCTTTGCATGGTAG/CAATGCACGTGGCTGAGCCGAGCTGTGGTACTGGCCAGCAGCCGAGGCATCGCCAGCT
```

Figure 12B  Underlined region is SEQ ID 22 in SEQ ID 1

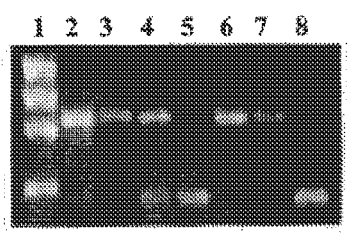

Figure 12C

SEQUENCE LISTING

<160> NUMBER OF SEQ ID NOS: 44

<210> SEQ ID NO 1
<211> LENGTH: 100
<212> TYPE: DNA
<213> ORGANISM: Homo sapiens

<400> SEQUENCE: 1
gcatgagttc actgagttcc ctttggcttt tccatgctag caatgcacgt ggcccagcct    60
gctgtggtac tggccagcag ccgaggcatc gccagctttg                          100

<210> SEQ ID NO 2
<211> LENGTH: 60
<212> TYPE: DNA
<213> ORGANISM: Homo sapiens

<400> SEQUENCE: 2
caatgcacgt ggcccagcct gctgtggtac tggccagcag ccgaggcatc gccagctttg    60

<210> SEQ ID NO 3
<211> LENGTH: 40
<212> TYPE: DNA
<213> ORGANISM: Homo sapiens

```
<400> SEQUENCE: 3
gcatgagttc actgagttcc ctttggcttt tccatgctag                              40

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
gcaggctggg ccacgtgcat tg                                                 22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
cacgtgcatt gctagcatgg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ctagcatgga aaagccaaag                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ggaactcagt gaactcatgc                                                    20

<210> SEQ ID NO 8
<211> LENGTH: 100
<212> TYPE: DNA
<213> ORGANISM: Mus musculus

<400> SEQUENCE: 8
tcatgagccc actaagtgcc ctttggactt tccatgtcag ccatacaggt gacccaacct        60
tcagtggtgt tggctagcag ccatggtgtc gccagctttc                             100

<210> SEQ ID NO 9
<211> LENGTH: 60
<212> TYPE: DNA
<213> ORGANISM: Mus musculus

<400> SEQUENCE: 9
ccatacaggt gacccaacct tcagtggtgt tggctagcag ccatggtgtc gccagctttc        60

<210> SEQ ID NO 10
<211> LENGTH: 40
<212> TYPE: DNA
<213> ORGANISM: Mus musculus
```

```
<400> SEQUENCE: 10
tcatgagccc actaagtgcc ctttggactt tccatgtcag                              40

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
ggttgggtca cctgtatgg                                                     19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
ccgggcatgg ttctggatc                                                     19

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
gtaaggcggt gggtacatg                                                     19

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
catcttgctc aaagaaacag                                                    20

<210> SEQ ID NO 15
<211> LENGTH: 12
<212> TYPE: PRT
<213> ORGANISM: Artificial Sequence
<220> FEATURE:
<223> OTHER INFORMATION: Synthetic arginine-rich peptide

<400> SEQUENCE: 15

Arg Arg Arg Arg Arg Arg Arg Arg Arg Phe Phe Cys
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(13)
<223> OTHER INFORMATION: Xaa is 6-aminohexanoic acid
<220> FEATURE:
<221> NAME/KEY: MOD_RES
```

```
<222> LOCATION: (14)..(14)
<223> OTHER INFORMATION: Xaa is beta-alanine

<400> SEQUENCE: 16

Arg Xaa Arg Arg Xaa Arg Xaa Arg Xaa Arg Xaa Xaa
 1               5                  10

<210> SEQ ID NO 17
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(16)
<223> OTHER INFORMATION: Xaa is 6-aminohexanoic acid
<220> FEATURE:
<221> NAME/KEY: MOD_RES
<222> LOCATION: (17)..(17)
<223> OTHER INFORMATION: Xaa is beta-alanine

<400> SEQUENCE: 17

Arg Xaa Arg Xaa Arg Xaa Arg Xaa Arg Xaa Arg Xaa Arg Xaa Arg Xaa
 1               5                  10                  15

Xaa

<210> SEQ ID NO 18
<211> LENGTH: 9
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(8)
<223> OTHER INFORMATION: Xaa is 6-aminohexanoic acid
<220> FEATURE:
<221> NAME/KEY: MOD_RES
<222> LOCATION: (9)..(9)
<223> OTHER INFORMATION: Xaa is beta-alanine

<400> SEQUENCE: 18

Arg Xaa Arg Xaa Arg Xaa Arg Xaa Xaa
 1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(7)
<223> OTHER INFORMATION: Xaa is 6-aminohexanoic acid
<220> FEATURE:
<221> NAME/KEY: MOD_RES
<222> LOCATION: (8)..(8)
<223> OTHER INFORMATION: Xaa is beta-alanine

<400> SEQUENCE: 19

Arg Xaa Arg Arg Xaa Arg Xaa Xaa
 1               5

<210> SEQ ID NO 20
<211> LENGTH: 16
<212> TYPE: PRT
<213> ORGANISM: Artificial Sequence
<220> FEATURE:
```

<223> OTHER INFORMATION: Synthetic arginine-rich peptide
<220> FEATURE:
<221> NAME/KEY: MOD_RES
<222> LOCATION: (2)..(16)
<223> OTHER INFORMATION: Xaa is beta-alanine

<400> SEQUENCE: 20

Arg Xaa Arg Xaa Arg Xaa Arg Xaa Arg Xaa Arg Xaa Arg Xaa Arg Xaa
 1               5                  10                  15

<210> SEQ ID NO 21
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: 2, 8, 13
<223> OTHER INFORMATION: Xaa is 6-aminohexanoic acid
<220> FEATURE:
<221> NAME/KEY: MOD_RES
<222> LOCATION: 5, 11, 14
<223> OTHER INFORMATION: Xaa is beta-alanine

<400> SEQUENCE: 21

Arg Xaa Arg Arg Xaa Arg Arg Xaa Arg Arg Xaa Arg Xaa Xaa
 1               5                  10

<210> SEQ ID NO 22
<211> LENGTH: 42
<212> TYPE: DNA
<213> ORGANISM: Homo sapiens

<400> SEQUENCE: 22
ctttggcttt tccatgctag caatgcacgt ggcccagcct gc                         42

<210> SEQ ID NO 23
<211> LENGTH: 19
<212> TYPE: DNA
<213> ORGANISM: Homo sapiens

<400> SEQUENCE: 23
catggaaagt ccaaagggc                                                   19

<210> SEQ ID NO 24
<211> LENGTH: 107
<212> TYPE: PRT
<213> ORGANISM: Artificial Sequence
<220> FEATURE:
<223> OTHER INFORMATION: Altered CTLA-4 using splice altering PMO

<400> SEQUENCE: 24

Met Ala Cys Leu Gly Leu Arg Arg Tyr Lys Ala Gln Leu Gln Leu Pro
 1               5                  10                  15

Ser Arg Thr Trp Pro Phe Val Ala Leu Leu Thr Leu Leu Phe Ile Pro
                20                  25                  30

Val Phe Ser Glu Asp Pro Glu Pro Cys Pro Asp Ser Asp Phe Leu Leu
            35                  40                  45

Trp Ile Leu Val Ala Val Ser Leu Gly Leu Phe Phe Tyr Ser Phe Leu
        50                  55                  60

Val Thr Ala Val Ser Leu Ser Lys Met Leu Lys Lys Arg Ser Pro Leu
65                  70                  75                  80

Thr Thr Gly Val Tyr Val Lys Met Pro Pro Thr Glu Pro Glu Cys Glu
                85                  90                  95

```
Lys Gln Phe Gln Pro Tyr Phe Ile Pro Ile Asn
                100                 105

<210> SEQ ID NO 25
<211> LENGTH: 36
<212> TYPE: PRT
<213> ORGANISM: Homo sapiens

<400> SEQUENCE: 25

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Phe Ile Pro
            20                  25                  30

Val Phe Ser Glu
        35

<210> SEQ ID NO 26
<211> LENGTH: 71
<212> TYPE: PRT
<213> ORGANISM: Homo sapiens

<400> SEQUENCE: 26

Asp Pro Glu Pro Cys Pro Asp Ser Asp Phe Leu Leu Trp Ile Leu Val
1               5                   10                  15

Ala Val Ser Leu Gly Leu Phe Phe Tyr Ser Phe Leu Val Thr Ala Val
            20                  25                  30

Ser Leu Ser Lys Met Leu Lys Lys Arg Ser Pro Leu Thr Thr Gly Val
            35                  40                  45

Tyr Val Lys Met Pro Pro Thr Glu Pro Glu Cys Glu Lys Gln Phe Gln
        50                  55                  60

Pro Tyr Phe Ile Pro Ile Asn
65                  70

<210> SEQ ID NO 27
<211> LENGTH: 174
<212> TYPE: PRT
<213> ORGANISM: Artificial Sequence
<220> FEATURE:
<223> OTHER INFORMATION: Altered CTLA-4 using splice altering PMO

<400> SEQUENCE: 27

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
                100                 105                 110

Asn Leu Thr Ile Gln Gly Leu Arg Ala Val Asp Thr Gly Leu Tyr Leu
            115                 120                 125

Cys Lys Val Glu Leu Met Tyr Pro Pro Pro Tyr Phe Val Gly Met Gly
```

```
                130              135              140
Asn Gly Thr Gln Ile Tyr Val Ile Ala Lys Glu Lys Ser Ser Tyr
145                 150                 155                 160

Asn Arg Gly Leu Cys Glu Asn Ala Pro Asn Arg Ala Arg Met
                165                 170

<210> SEQ ID NO 28
<211> LENGTH: 174
<212> TYPE: PRT
<213> ORGANISM: Rattus norvegicus

<400> SEQUENCE: 28

Met Ala Cys Leu Gly Leu Gln Arg Tyr Lys Thr His Leu Gln Leu Pro
 1               5                  10                  15

Ser Arg Thr Trp Pro Phe Gly Val Leu Leu Ser Leu Leu Phe Ile Pro
             20                  25                  30

Ile Phe Ser Glu Ala Ile Gln Val Thr Gln Pro Ser Val Val Leu Ala
         35                  40                  45

Ser Ser His Gly Val Ala Ser Phe Pro Cys Glu Tyr Ala Ser Ser His
     50                  55                  60

Asn Thr Asp Glu Val Arg Val Thr Val Leu Arg Gln Thr Asn Asp Gln
65                  70                  75                  80

Val Thr Glu Val Cys Ala Thr Thr Phe Thr Val Lys Asn Thr Leu Gly
                 85                  90                  95

Phe Leu Asp Asp Pro Phe Cys Ser Gly Thr Phe Asn Glu Ser Arg Val
            100                 105                 110

Asn Leu Thr Ile Gln Gly Leu Arg Ala Ala Asp Thr Gly Leu Tyr Phe
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Ala Lys Glu Lys Ser Ser Tyr
145                 150                 155                 160

Asn Arg Gly Leu Cys Glu Asn Ala Pro Asn Arg Ala Arg Met
                165                 170

<210> SEQ ID NO 29
<211> LENGTH: 101
<212> TYPE: DNA
<213> ORGANISM: Mus musculus

<400> SEQUENCE: 29
gatcatgagc ccactaagtg cccttttggac tttccatgtc agccatacag gtgacccaac      60
cttcagtggt gttggctagc agccatggtg tcgccgcttt c                         101

<210> SEQ ID NO 30
<211> LENGTH: 96
<212> TYPE: DNA
<213> ORGANISM: Homo sapiens

<400> SEQUENCE: 30
gcatgagttc actgagttcc ctttggcttt tccatgctag caatgcacgt ggcccagcct      60
gctgtggtac tggccagcag ccgaggcatc gccagc                                96

<210> SEQ ID NO 31
<211> LENGTH: 20
<212> TYPE: DNA
<213> ORGANISM: Artificial Sequence
<220> FEATURE:
```

```
<223> OTHER INFORMATION: Synthetic oligonucleotide

<400> SEQUENCE: 31
ccaagacaag ccatggctgg                                            20

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
acacatatgt agcacgtacc ttgga                                      25

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
ggaattttgc atccagcttt ctat                                       24

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
aagccgtact tctgccgt                                              18

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
ccacaacgaa agctgcac                                              18

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
atgacactca ggctgctg                                              18

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
gcaagccata acaaaacag                                             19
```

```
<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
actcatgtac ccaccgcca                                                  19

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
gggcatggtt ctggatca                                                   18

<210> SEQ ID NO 40
<211> LENGTH: 25
<212> TYPE: DNA
<213> ORGANISM: Artificial Sequence
<220> FEATURE:
<223> OTHER INFORMATION: flCTLA-4 probe

<400> SEQUENCE: 40
catgggcaac gggacgcaga tttat                                           25

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41 gcctttgta gccctgctca                                                  20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
tcagaatccg ggcatggtt                                                  19

<210> SEQ ID NO 43
<211> LENGTH: 32
<212> TYPE: DNA
<213> ORGANISM: Artificial Sequence
<220> FEATURE:
<223> OTHER INFORMATION: liCTLA-4 probe

<400> SEQUENCE: 43 ttctttcat cccagtcttc tctgaagatc ca                                    32

<210> SEQ ID NO 44
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
```

```
<221> NAME/KEY: MOD_RES
<222> LOCATION: (12)..(12)
<223> OTHER INFORMATION: Xaa is 6-aminohexanoic acid
<220> FEATURE:
<221> NAME/KEY: MOD_RES
<222> LOCATION: (13)..(13)
<223> OTHER INFORMATION: Xaa is beta-alanine

<400> SEQUENCE: 44

Arg Arg Arg Arg Arg Arg Arg Arg Arg Phe Phe Xaa Xaa
 1               5                  10
```

IMMUNOSUPPRESSION COMPOUND AND TREATMENT METHOD

CROSS-REFERENCE TO RELATED APPLICATIONS

This application is a continuation of U.S. application Ser. No. 12/267,437 filed Nov. 7, 2008 (allowed); which is a continuation-in-part of U.S. application Ser. No. 11/595,161 filed Nov. 8, 2006 (abandoned); which claims the benefit of U.S. Provisional Application No. 60/735,000 filed Nov. 8, 2005, and U.S. Provisional Application No. 60/799,976 filed May 11, 2006, all of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_440C3_SEQUENCE_LISTING.txt. The text file is 13.3 KB, was created on Mar. 3, 2015, and is being submitted electronically via EFS-Web.

FIELD OF THE INVENTION

The present invention relates to methods and antisense oligonucleotide analog compounds useful in suppressing an immune response in a mammalian subject, for the treatment and/or prevention of autoimmune conditions and transplantation rejection.

REFERENCES

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Anderson, C. M., W. Xiong, et al. (1999). "Distribution of equilibrative, nitrobenzylthioinosine-sensitive nucleoside transporters (ENT1) in brain." *J Neurochem* 73(2): 867-73.

Anderson, K. P., M. C. Fox, et al. (1996). "Inhibition of human cytomegalovirus immediate-early gene expression by an antisense oligonucleotide complementary to immediate-early RNA." *Antimicrob Agents Chemother* 40(9): 2004-11.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Ding, D., S. M. Grayaznov, et al. (1996). "An oligodeoxyribonucleotide N3'-->P5' phosphoramidate duplex forms an A-type helix in solution." *Nucleic Acids Res* 24(2): 354-60.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Hudziak, R. M., E. Barofsky, et al. (1996). "Resistance of morpholino phosphorodiamidate oligomers to enzymatic degradation." *Antisense Nucleic Acid Drug Dev* 6(4): 267-72.

Loke, S. L., C. A. Stein, et al. (1989). "Characterization of oligonucleotide transport into living cells." *Proc Natl Acad Sci USA* 86(10): 3474-8.

Moulton, H. M., M. C. Hese, et al. (2003). "HIV Tat peptide enhances cellular delivery of antisense morpholino oligomers." *Antisense Nucleic Acid Drug Dev* 13(1): 31-43.

Moulton, H. M. and J. D. Moulton (2003). "Peptide-assisted delivery of steric-blocking antisense oligomers." *Curr Opin Mol Ther* 5(2): 123-32.

Moulton, H. M., M. H. Nelson, et al. (2004). "Cellular uptake of antisense morpholino oligomers conjugated to arginine-rich peptides." *Bioconjug Chem* 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

Pari, G. S., A. K. Field, et al. (1995). "Potent antiviral activity of an antisense oligonucleotide complementary to the intron-exon boundary of human cytomegalovirus genes UL36 and UL37," *Antimicrob Agents Chemother* 39(5): 1157-61.

Stein, D., E. Foster, et al. (1997), "A specificity comparison of four antisense types: morpholino, 2'-O-methyl RNA, DNA, and phosphorothioate DNA." *Antisense Nucleic Acid Drug Dev* 7(3): 151-7.

Summerton, J. and D. Weller (1997). "Morpholino antisense oligomers: design, preparation, and properties." *Antisense Nucleic Acid Drug Dev* 7(3): 187-95.

Toulme, J. J., R. L. Tinevez, et al. (1996), "Targeting RNA structures by antisense oligonucleotides." *Biochimie* 78(7): 663-73.

Vijayakrishnan, L., J. M. Slavik, et al. (2004), "An autoimmune disease-associated CTLA-4 splice variant lacking the B7 binding domain signals negatively in T cells." *Immunity* 20(5): 563-75.

Wender, P. A., D. J. Mitchell, et al. (2000). "The design, synthesis, and evaluation of molecules that enable or enhance cellular uptake: peptoid molecular transporters." *Proc Natl Acad Sci USA* 97(24): 13003-8.

Yakubov, L. A., E. A. Deeva, et al. (1989). "Mechanism of oligonucleotide uptake by cells: involvement of specific receptors?" *Proc Natl Acad Sci USA* 86(17): 6454-8.

BACKGROUND OF THE INVENTION

Under normal circumstances, the immune system exhibits immune tolerance (i.e. lack of immune responsiveness) to self-antigens. Abnormalities in soft-tolerance lead to immune responses against self and debilitating inflammatory disorders commonly called autoimmune diseases. These include rheumatoid arthritis, type I diabetes, systemic lupus erythematosis, inflammatory bowel disease (e.g., Crohn's disease), myasthenia gravis, multiple sclerosis, among many others. Current therapy has variable success and is fraught with risks of over-immunosuppression. Therefore, there is a need for improved immunosuppressive agents that are more effective in treating autoimmune disorders. More effective immunomodulatory agents, particularly those able to restore immunologic tolerance, would therefore be of great benefit.

Transplantation is the current treatment of choice for end-stage heart, kidney, and liver disease. Although improved post-transplant immunosuppression has led to excellent short-term allograft survival, acute rejection still occurs and long-term results remain inadequate. Moreover, sub-clinical rejection is still relatively frequent on protocol biopsies and may contribute to chronic rejection. Finally, current therapy requires life-long immunosuppression with attendant risks of infection and malignancy.

Therefore, there is a need for improved immunosuppressive agent that are both more effective and more specific for prevention of rejection (with less generalized immunosuppression and side-effects). The ideal therapy would consist of a finite course of treatment that would induce specific tolerance (lack of responsiveness) for the transplant, while leaving the immune system intact to defend against other threats. Achieving tolerance would reduce rejection, increase long-term engraftment, and eliminate continuous immunosuppression, thereby reducing morbidity, mortality, and cost.

SUMMARY OF THE INVENTION

The invention includes, in one aspect, a composition for suppressing an immune response in a subject, for the treatment or prevention of an autoimmune condition. The composition includes (a) a pharmaceutically effective amount of compound composed of (i) a morpholino antisense oligonucleotide antisense compound composed of (i) a morpholino antisense oligonucleotide having between 12 and 40 morpholino subunits and phosphorus-containing intersubunit linkages joining a morpholino nitrogen of one subunit to a 5'-exocycklic carbon of an adjacent subunit and having a targeting sequence that contains at least 12 contiguous bases that are complementary to SEQ ID 22, the region of SEQ ID NO: 1 targeted by one or more of the overlapping sequences identified by SEQ ID NOS: 4-6, where the oligonucleotide is capable of forming with pre-processed CTLA-4 mRNA, a heteroduplex structure characterized by a Tm of dissociation of at least 45° C.; and (b) a pharmaceutically acceptable carrier.

The morpholino subunits in the antisense oligonucleotide may be joined by phosphorodiamidate linkages, in accordance with the structure:

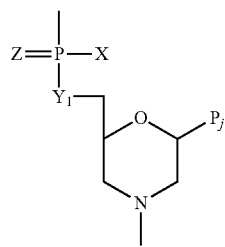

where $Y_1$=O, Z=O, Pj is a purine or pyrimidine base-pairing moiety effective to bind, by base-specific hydrogen bonding, to a base in a polynucleotide, and X is an alkyl amine of form the $NR_2$, where R is methyl or H.

In one embodiment, at least 2 and no more than half of the total number of intersubunit linkages in the antisense oligonucleotide are positively charged at physiological pH, and the morpholino subunits are joined by phosphorodiamidate linkages, in accordance with the structure:

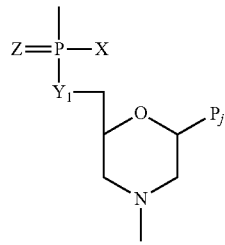

where $Y_1$=O, Z=O, Pj is a ovine or pyrimidine base-pairing moiety effective to bind, by base-specific hydrogen bonding, to a base in a polynucleotide, and X for the uncharged linkages is an alkyl amine of the form $NR_2$, where each R is independently hydrogen or methyl, and for the positively charged linkages, X is 1-piperazine.

The arginine-rich peptide in the compound has one of the sequences identified as SEQ ID NOS:15-21. Exemplary sequences are SEQ ID NOS:16 and 21.

The oligonucleotide may be contained within includes one or more of the overlapping sequences identified as SEQ ID NOS: 4-6. An exemplary oligonucleotide has the sequence SEQ ID NO: 4.

In another aspect, the invention includes a method of inducing immunological tolerance in a subject, for the prevention or treatment of an autoimmune condition. The method includes administering to the subject, a pharmaceutically effective amount of an antisense compound described above, monitoring the subject by tests appropriate to the condition being treated, and repeating the administering step until improvement in the disorder is observed.

The antisense compound may be administered by a parenteral route, such as intravenous or intraperitoneal administration, in an amount between 5-250 mg compound/dose.

The oligonucleotide in the administered compound may have a sequence contained in one or more of the overlapping sequences identified as SEQ ID NOS: 4-6. The arginine-rich peptide in the compound administered may have the sequence identified by SEQ ID NOS: 15-21, e.g., SEQ ID NOS: 16 or 21.

The method may be used for delaying the onset of Type-1 diabetes in a subject, wherein monitoring the subject in step (b) includes measuring the blood sugar levels of the subject.

These and other objectives and features of the invention full be more fully appreciated when the following detailed description of the invention is read in conjunction with the accompanying drawings.

BRIEF DESCRIPTION OF THE FIGURES

FIG. 5 shows an examination of the alterations made to the CTLA-4 mRNA sequence after treatment with splice altering PMOs; SA2/SD2 is SEQ ID NO:24; CTLA-4 is SEQ ID NOS:25 and 26; SD/SA3 is SEQ ID NO:27; and 090271 is SEQ ID NO:28;

FIGS. 12A and 12C show antisense oligomers targeting different regions surrounding the intron 1 exon 2 pre-mRNA boundary of murine CTLA-4 (SEQ ID NO:29); where the oligomers identified by numbers 4 and 5 correspond to SEQ ID NOS: 23 and 11, respectively (12A); corresponding antisense oligomers targeting different regions surrounding the intron 1 exon 2 pre-mRNA boundary of human CTLA-4 (SEQ ID NO:30), identified by SEQ ID numbers (12B), and gel electrophoretic bands of RNA isolated from cultured NOD splenocytes treated with the various PPMOs from FIG. 12A (12C).

DETAILED DESCRIPTION OF THE INVENTION

I. Definitions

Figure 1A:
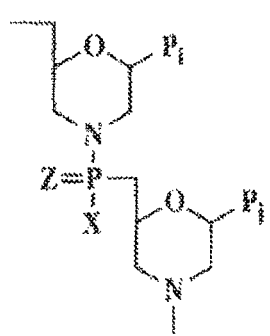
FIGS. 1A-1D show the repeating subunit segment of several preferred morpholino oligonucleotides, designated A through D, constructed using subunits having 5-atom (A), six-atom (B) and seven-atom (C-D) linking groups suitable for forming polymers.

The terms below, as used herein, have the following meanings, unless indicated otherwise.

The terms "CTLA-4" and "CD152" refer to the cytotoxic T cell antigen-4, a molecule expressed primarily by T lymphocytes that is involved in regulation of the immune response and in the generation of immune tolerance (specific non-responsiveness) in transplantation and autoimmunity. The outcome of T cell activation is determined by signals from the antigen receptor and opposing, costimulatory signals from CD28 and inhibitory signals from CTLA-4 that are integrated by the T-cell in determining the response to antigen.

The terms "immunosuppression" and "immunological tolerance" refer to the formation of T cells that are conditioned, using the methods and compositions of the invention, to induce a T-cell response that suppresses antigen-specific immunity.

The term "CTLA-4 mRNA isoforms" refer to the various alternatively spliced mRNA species of the CTLA-4 gene that either occur naturally or that are induced using the compounds and methods of the invention.

The terms "antisense oligonucleotides," "antisense oligomer," and "antisense compound" are used interchangeably and refer to a compound having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The antisense oligonucleotide includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions that allow such hydrogen bonding. These backbone moieties are cyclic moieties of 5 to 7 atoms in length, linked together by phosphorous-containing linkages one to three atoms long.

A "morpholino" oligonucleotide refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 1A-1D, where (i) the structures are linked together by phosphorous-containing linkages, one to three atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 1A-1D, with the uncharged, phosphorous-containing linkages shown in FIGS. 1A-1D, and more generally, the uncharged linkages 2A-2G.

As used herein, an oligonucleotide or antisense oligomer "specifically hybridizes" to a target polynucleotide if the oligomer hybridizes to the target under physiological conditions, with a thermal melting point (Tm) substantially greater than 37° C., preferably at least 45° C., and typically 50° C.-80° C. or higher. Such hybridization preferably corresponds to stringent hybridization conditions, selected to be about 10° C., and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules. An antisense compound may be complementary to a target region of a target transcript even if the two base sequences are not 100% complementary, for example if they are 80% complementary or 90% complementary, as long as the heteroduplex structure formed between the compound and transcript has the desired Tm stability, where the degree of complementarity required for stable hybridization would depend on the total number of bases involved, the ratio of G:C to A:T base matches, and other factors known to those of skill in the art.

As used herein the term "analog" with reference to an oligomer means a substance possessing both structural and chemical properties similar to those of the reference oligomer.

A substantially uncharged, phosphorus containing backbone in an oligonucleotide analog is one in which a majority of the subunit linkages, e.g., between 50-100%, are uncharged at physiological pH, and contain a single phosphorous atom. The analog contains between 12 and 40 subunits, typically about 15-25 subunits, and preferably about 18 to 25 subunits. The analog may have exact sequence complementarity to the target sequence or near complementarity, as defined above.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

Figure 2A:
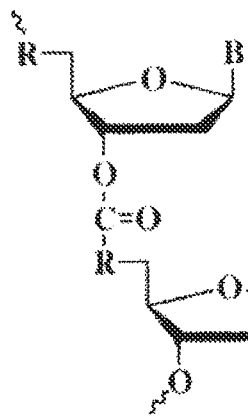
FIGS. 2A-2G show examples of uncharged linkage types in oligonucleotide analogs.
Figure 2B:
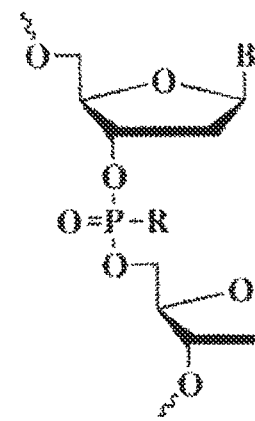
Figure 2C:
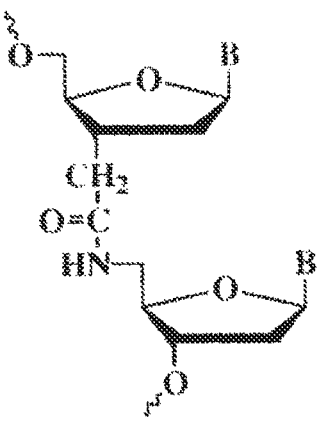
Figure 2D:
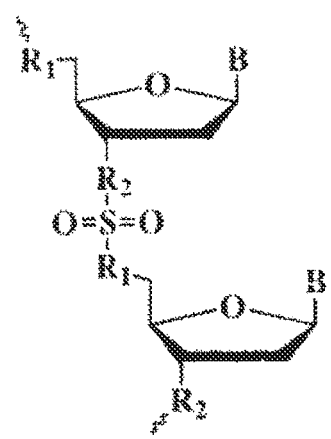
Figure 2E:
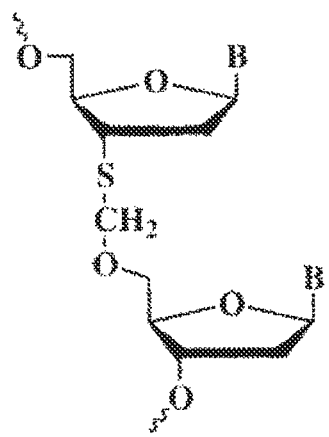
Figure 2F:
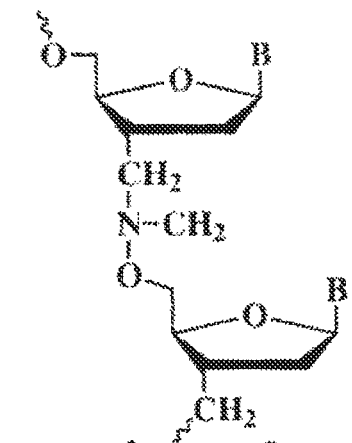
Figure 2G:
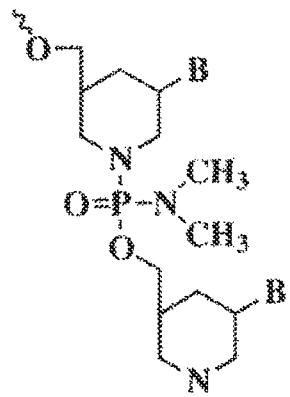
Figure 2H:
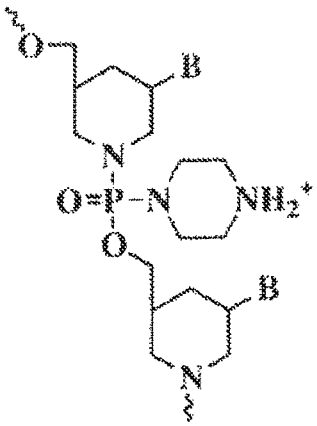
FIG. 2H shows an example of a preferred cationic linkage group.

A preferred morpholino oligomer is a phosphorodiamidate-linked morpholino oligomer, referred to herein as a PMO. Such oligomers are composed of morpholino subunit structures such as shown in FIG. 2B, where X=NH2, NHR, or NR2 (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2G. Also preferred are morpholino oligomers where the phosphordiamidate linkages are uncharged linkages as shown in FIG. 2G interspersed with cationic linkages as shown in FIG. 2H where, in FIG. 2B, X=1-piperazino. In another FIG. 2B embodiment, X=lower alkoxy, such as methoxy or ethoxy, Y=NH or NR, where R is lower alkyl, and Z=O.

As used herein, a first sequence is an "antisense sequence" or "targeting sequence" with respect to a second sequence or "target sequence" if a polynucleotide whose sequence is the first sequence specifically binds to, or specifically hybridizes with, the second polynucleotide sequence under physiological conditions.

As used herein, "effective amount" relative to an antisense oligomer refers to the amount of antisense oligomer administered to a subject, either as a single dose or as part of a series of doses that is effective to inhibit expression of a selected target nucleic acid sequence.

II. Antisense Compound for Targeting T Cells

A. Antisense Compound

Antisense oligomers for use in practicing the invention preferably have the following properties: (1) a backbone that is substantially uncharged, (2) the ability to hybridize with the complementary sequence of a target RNA with high affinity, that is a Tm substantially greater than 37° C., preferably at least 45° C., and typically greater than 50° C., e.g., 60° C.-80° C. or higher, (3) a subunit length of at least 8 bases, generally about 8-40 bases, preferably 12-25 bases, and (4) nuclease resistance (Hudziak, Barofsky et al., 1996). In addition, the antisense compound may have the capability for active or facilitated transport as evidenced by (i) competitive binding with a phosphorothioate antisense oligomer, and/or (ii) the ability to transport a detectable reporter into target cells.

Candidate antisense oligomers may be evaluated, according to well known methods, for acute and chronic cellular toxicity, such as the effect on protein and DNA synthesis as measured via incorporation of 3H-leucine and 3H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests is important in discerning specific effects of antisense inhibition of gene expression from indiscriminate suppression. Accordingly, sequences may be modified as needed to limit non-specific binding of antisense oligomers to non-target nucleic acid sequences.

Heteroduplex Formation

The effectiveness of a given antisense oligomer molecule in forming a heteroduplex with the target mRNA may be determined by screening methods known in the art. For example, the oligomer is incubated in a cell culture containing an mRNA preferentially expressed in activated lymphocytes, and the effect on the target mRNA is evaluated by monitoring the presence or absence of (1) heteroduplex formation with the target sequence and non-target sequences using procedures known to those of skill in the art, (2) the amount of the target mRNA expressed by activated lymphocytes, as determined by standard techniques such as RT-PCR or Northern blot, (3) the amount of protein transcribed from the target mRNA, as determined by standard techniques such as ELISA or Western blotting. (See, for example, (Pari, Field et al. 1995; Anderson, Fox et al. 1996).

For the purposes of the invention, a preferred test for the effectiveness of the CTLA-4 antisense oligomer is by measuring CTLA-4 mRNA isoform expression in mature T cells treated with the antisense CTLA-4 oligomer.

Uptake into Cells

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy or FACS analysis, for intracellular label. The presence of significant intracellular label is evidence that the test compound is transported by facilitated or active transport.

In one embodiment of the invention, uptake into cells is enhanced by administering the antisense compound in combination with an arginine-rich peptide linked to the 5' or 3' end of the antisense oligomer. The peptide is typically 8-16 amino acids and consists of a mixture of arginine, and other amino acids including phenylalanine, cysteine, 6-aminohexanoic acid (Ahx) and beta-alanine (βAla) as discussed further below. Exemplary arginine-rich peptides are listed as SEQ ID NOs: 15-20.

RNAse Resistance

Two general mechanisms have been proposed to account for inhibition of expression by antisense oligonucleotides (Agrawal, Mayrand et al. 1990; Bonham, Brown et al. 1995; Boudvillain, Guerin at al. 1997). In the first, a heteroduplex formed between the oligonucleotide and the viral RNA acts as a substrate for RNaseH, leading to cleavage of the RNA. Oligonucleotides belonging, or proposed to belong, to this class include phosphorothioates, phosphotriesters, and phosphodiesters (unmodified "natural" oligonucleotides). Such compounds expose the RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and act by sterically blocking target RNA nucleocytoplasmic transport, splicing, translation, or replication. This class includes methylphosphonates (Toulme, Tinevez at al. 1996), morpholino oligonucleotides, peptide nucleic acids (PNA's), certain 2'-O-allyl or 2'-O-alkyl modified oligonucleotides (Bonham, Brown et al. 1995), and N3'☐P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described (Stein, Foster et al.

1997). After exposure to RNaseH, the presence or absence of intact duplex can be monitored by gel electrophoresis or mass spectrometry.

In Vivo Uptake

In accordance with another aspect of the invention, there is provided a simple, rapid test for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the CD86 preprocessed or processed RNA target when administered to a mammalian subject, and the heteroduplex subsequently appears in the urine (or other body fluid). Details of this method are also given in co-owned U.S. Pat. No. 6,385,351 for "Non-Invasive Method for Detecting Target RNA," the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including RNA encoded by a host gene. Several hours (typically 8-72) after administration, the urine is assayed for the presence of the antisense-RNA heteroduplex. If the heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Structural Features

As detailed above, the antisense oligomer has a base sequence directed to a targeted portion of a cellular gene, preferably the region at or adjacent to a splice site junction of the CTLA-4 mRNA or preprocessed transcript. In addition, the oligomer is able to effectively inhibit expression of the targeted gene when administered to a host cell, e.g. in a mammalian subject. This requirement is met when the oligomer compound (a) has the ability to be taken up by T cells and (b) once taken up, form a duplex with the target RNA with a Tm greater than about 45° C., preferably greater than 50° C.

The ability to be taken up selectively by T cells requires, in part, that the oligomer backbone be substantially uncharged. The ability of the oligomer to form a stable duplex with the target RNA will depend on the oligomer backbone, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm and/or nucleus.

Antisense oligonucleotides of 15-20 bases are generally long enough to have one complementary sequence in the mammalian genome. In addition, antisense compounds having a length of at least 12, typically at least 15 nucleotides in length hybridize well with their target mRNA. Due to their hydrophobicity, antisense oligonucleotides tend to interact well with phospholipid membranes, and it has been suggested that following the interaction with the cellular plasma membrane, oligonucleotides are actively transported into living cells (Lake, Stein et al., 1989; Yakubov, Deeva at al. 1989; Anderson, Xiong et al., 1999).

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

Morpholino oligonucleotides, particularly phosphoramidate- or phosphorodiamidate-linked morpholine oligonucleotides have been shown to have high binding affinities for complementary or near-complementary nucleic acids. Morpholino oligomers also exhibit little or no non-specific antisense activity, afford good water solubility, are immune to nucleases, and are designed to have low production costs (Summerton and Weller 1997).

Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein In one preferred approach, antisense oligomers for use in practicing the invention are composed of morpholino subunits of the form shown in the above cited patents, where (i) the morpholino groups are linked together by uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil, thymine or inosine. Preparation of such oligomers is described in detail in U.S. Pat. No. 5,185,444 (Summerton et al., 1993), which is hereby incorporated by reference in its entirety. As shown in this reference, several types of nonionic linkages may be used to construct a morpholino backbone.

The antisense activity of the oligomer may be enhanced by using a mixture of uncharged and cationic phosphorodiamidate linkages as shown in FIGS. 2G and 2H. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Exemplary subunit structures for antisense oligonucleotides of the invention include the morpholino subunit types shown in FIGS. 1A-D, each linked by an uncharged, phosphorous-containing subunit linkage, also shown in FIGS.

1A-1D. In these figures, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1-6 carbon atoms, and more preferably 1-4 carbon atoms. Monosubstituted or disubstituted nitrogen preferably refers to lower alkyl substitution, and the cyclic structures are preferably 5- to 7-membered nitrogen heterocycles optionally containing 1-2 additional heteroatoms selected from oxygen, nitrogen, and sulfur. Z is sulfur or oxygen, and is preferably oxygen.

Figure 1B:
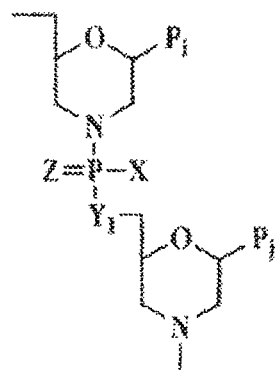

FIG. 1A shows a phosphorous-containing linkage which forms the five atom repeating-unit backbone shown in FIG. 1A, where the morpholino rings are linked by a 1-atom phosphoamide linkage. Subunit B in FIG. 1B is designed for 6-atom repeating-unit backbones, as shown in FIG. 1B. In FIG. 1B, the atom Y inking the 5' morpholino carbon to the phosphorous group may be sulfur, nitrogen, carbon or, preferably, oxygen. The X moiety pendant from the phosphorous may be any of the following; fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Z is sulfur or oxygen, and is preferably oxygen. Particularly preferred morpholino oligonucleotides include those composed of morpholino subunit structures of the form shown in FIG. 1B, where X is an amine or alkyl amine of the form $X=NR_2$, where R is independently H or $CH_3$, that is where $X=NH_2$, $X=NHCH_3$ or $X=N(CH_3)_2$, $Y=O$, and $Z=O$.

Figure 1C:
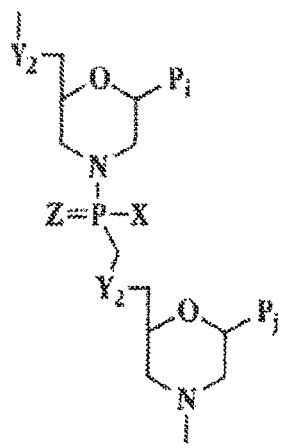
Figure 1D:
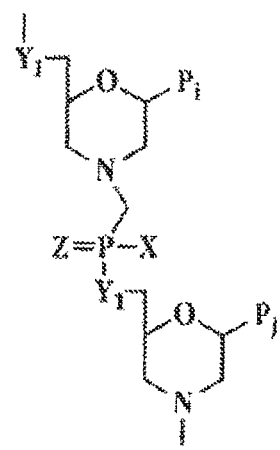

Subunits C-D in FIGS. 1C-D are designed for 7-atom unit-length backbones as shown for structures in FIGS. 1C and 1D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine, thymine, inosine and uracil.

As noted above, the substantially uncharged oligomer may advantageously include a limited number of charged backbone linkages. One example of a cationic charged phosphordiamidate linkage is shown in FIG. 2H. This linkage, in which the dimethylamino group shown in FIG. 2G is replaced by a 1-piperazino group as shown in FIG. 2H, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

More generally, oligomers with uncharged backbones are shown in FIGS. 2A-2G. Especially preferred is a substantially uncharged morpholino oligomer such as illustrated by the phosphorodiamidate morpholino oligomer (PMO) shown in FIG. 2G. It will be appreciated that a substantially uncharged backbone may include one or more, e.g., up to 10-20% of charged intersubunit linkages, typically negatively charged phosphorous linkages. An example of a cationic linkage is shown in FIG. 2H, wherein the nitrogen pendant to the phosphate atom in the linkage of FIG. 2G is replaced with a 1-piperazino structure. The method for synthesizing the 1-piperazino group linkages is described below with respect to FIG. 11.

Antisense Sequence

In the methods of the invention, the antisense oligomer is designed to hybridize to a region of the target nucleic acid sequence, under physiological conditions with a Tm substantially greater than 37° C., e.g., at least 45° C. and preferably 60° C.-80° C., wherein the target nucleic acid sequence is a processed or preprocessed mRNA preferentially expressed in T cells. The oligomer is designed to have high-binding affinity to the target nucleic acid sequence and may be 100% complementary thereto, or may include mismatches, e.g., to accommodate allelic variants, as long as the heteroduplex formed between the oligomer and the target nucleic acid sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to a nucleic acid sequence that is preferentially expressed in T cells, it is effective to stably and specifically bind to the target sequence such that expression of the target sequence is modulated. The appropriate length of the oligomer to allow stable, effective binding combined with good specificity is about 8-40 nucleotide base units, and preferably about 12-25 nucleotides. Oligomer bases that allow degenerate base pairing with target bases are also contemplated, assuming base-pair specificity with the target is maintained.

The antisense compounds for use in practicing the invention can be synthesized by stepwise solid-phase synthesis, employing methods detailed in the references cited above. The sequence of subunit additions will be determined by the selected base sequence. In some cases, it may be desirable to add additional chemical moieties to the oligomer compounds, e.g. to enhance the pharmacokinetics of the compound or to facilitate capture or detection of the compound. Such a moiety may be covalently attached, typically to the 5'- or 3'-end of the oligomer, according to standard synthesis methods. For example, addition of a polyethyleneglycol moiety or other hydrophilic polymer, e.g., one having 10-100 polymer subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection.

Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by cells in vitro or in vivo without undesirable side effects.

B. Arginine-Rich Polypeptide Moiety

The use of arginine-rich peptide sequences conjugated to uncharged antisense compounds, e.g., PMO, has been shown to enhance cellular uptake in a variety of cells (Wender, Mitchell et al. 2000; Moulton, Hase et al. 2003; Moulton and Moulton 2003; Moulton, Nelson et al. 2004; Nelson, Stein et al. 2005) (Iversen, Moulton et al. U.S. Patent Application No. 60/466,703, now U.S. publication number 2004/0265879 A1, published Dec. 30, 2004, all of which are incorporated herein by reference.

In one embodiment of the invention, the antisense compound is covalently linked at its 3' or 5' end to an arginine rich-peptide effective to enhance uptake of the compound into T cells relative to uptake in the absence of the peptide. The arginine-rich peptide is detailed in the above references to Moulton et al., and described in U.S. publication number 2004/0265879 A1. Preferably, the peptide is composed of d-amino acids, l-amino acids, non-natural amino acids or a combination thereof. Exemplary arginine-rich peptides include those identified by SEQ ID NOS: 15-21, of which those identified as SEQ ID NOS: 16 and 21 are preferred.

The transport peptide may significantly enhance cell entry of attached uncharged oligomer compounds, relative to uptake of the compound in the absence of the attached transport moiety. Uptake is preferably enhanced at least twenty fold, and more preferably forty fold, relative to the unconjugated compound.

A further benefit of the transport moiety is its expected ability to stabilize a duplex between an antisense oligomer and its target nucleic acid sequence, presumably by virtue of electrostatic interaction between the positively charged transport moiety and the negatively charged nucleic acid. The number of charged subunits in the transporter is less than 14, as noted above, and preferably between 4 and 11, since too high a number of charged subunits may lead to a reduction in sequence specificity.

The transport moiety may also lower the effective concentration of an antisense oligomer to achieve antisense activity as measured in both tissue culture and cell-free systems. Cell-free translation systems provide an independent means to assess the enhanced effect of the transport moiety on the antisense oligomers ability to bind to its target and, through steric blocking, inhibit translation of downstream sequences.

III. Targeting and Antisense Sequences

Previous evidence suggests that CTLA-4 expression could only be augmented by full-scale T cell activation and initiation of the T cell into the cell cycle. The current invention is based upon the finding that CTLA-4 activity can be modulated in naïve and activated T cells by manipulating the relative ratios of specific spliced mRNA isoforms of the CTLA-4 gene to increase immunosuppression and immunologic tolerance. More specifically, it has been discovered that administration of an antisense compound that targets the splice region between intron-1 and exon-2 shifts the ratios of CTLA-4 mRNAs and CTLA-4 proteins from full length to ligand-independent forms, and that this shift is effective in treating an autoimmune condition or transplantation rejection, and in reducing the risk of transplantation rejection, on pretreating the subject prior to the transplantation operation.

Figure 3:
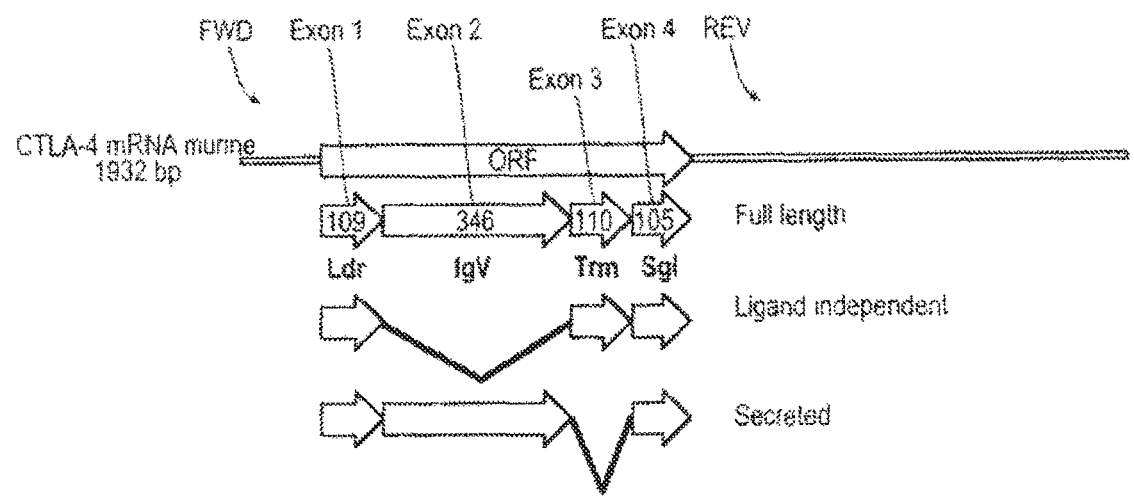
FIG. 3 shows full-length, ligand-independent, and secreted splice variant forms of CTLA-4.

FIG. 3 shows various splice variant isoforms of CTLA-4. As seen, the CTLA gene has four exon, designated exons 1-4, with an intron separating each axon pair. The introns are designated 1-3, where intron-1 is the intervening sequence between exons 1 and 2, intron-2, between axons 2 and 3, and intron-3, between axons 3 and 4. As shown, the full length CTLA isoform is encoded by all four exons, requiring excision of all three introns and preservation of all four exons. A ligand-independent form is of CTLA-4 is formed from axons 1, 3 and 4, requiring excision of intron 1 and adjacent exon 2, and introns 3 and 4. A secreted form of CTLA-4 is formed of exons 1, 2, and 4, requiring excision of intron 1, and a contiguous section of preprocessed mRNA containing intron 2, exon 3 and intron 3.

The antisense compound used in the method of the invention, and contained in the compound of the invention, has a base sequence that is complementary to at least 12 subunits that are complementary to SEQ ID NO: 1. An exemplary target region is the region of SEQ ID NO: 1 targeted by one or more of the overlapping sequences identified by SEQ ID NOS: 4-6. As seen in from the Table 1, and from FIG. 12B, this region of SEQ ID NO: 1 extends from a 5' end region complementary to SEQ ID NO: 6 to a 3'-end region complementary to SEQ ID NO: 4, and is identified herein as SEQ ID NO: 22. Exemplary antisense sequences targeting this region are those corresponding to SEQ ID NOS: 4-6.

However, other regions of the CTLA-4 mRNA may be targeted, including one or more of an initiator or promoter site, a 3'-untranslated region, and a 5'-untranslated region. Both spliced and unspliced, preprocessed RNA may serve as the template for design of antisense oligomers for use in the methods of the invention.

IV. Treating Transplantation Rejection and Autoimmune Disorder

By manipulating the immune system's normal mechanism for the generation of immune tolerance to self antigens, the present invention provides a method and composition that alters the function and activity of T cells in a way that is advantageous in the treatment of transplantation rejection or autoimmune disorders, such as multiple sclerosis, lupis, myathenia gravis, inflammatory bowel disease, rheumatoid arthritis, and Type 1 diabetes.

By employing an antisense oligomer against CTLA-4 (e.g., SEQ ID NOS: 4-6), the present invention provides a means to alter T cell activation in response to an antigen presented by a mature dendritic cell. This allows the generation of a tolerized T cell population responding to transplanted tissue, when chronically activated as in an autoimmune condition, or by an immunogenic therapeutic protein.

The generation of tolerized, anergic T-cells using the compounds and methods of the invention also provides a long-lasting tolerance that has a variety of therapeutic advantages.

A. CTLA-4 Splice-Altering Antisense Oligomers

Exemplary target and targeting sequences for the CD152 (CTLA-4) gene are listed below in Table 1 and Table 2, respectively. The human CTLA-4 mRNA, splice junction (sj), axon (ex), branch point (bp) and intron (in) target and targeting sequences are noted with "hu" and derived from Genbank Accession No. AF411058. The murine CTLA-4 (CD152) sequences are noted with "mu" and are derived from Genbank Accession No. AF142145. The "/" symbol indicates within the target sequences the intron 1/exon 2 splice site.

TABLE 1

Exemplary CTLA-4 Target Sequences

| Oligomer | TargetSequence (5' to 3') | Sp. | Net. Range | SEQ ID NO. |
|---|---|---|---|---|
| huCTLA-4SA2sj | GCATGAGTTCACTGAGTT CCCTTTGGCTTTTCCATG CTAGCAATGCACGTGGCC CAGCCTGCTGTGGTACTG GCCAGCAGCCGAGGCATC GCCAGCTTTG | hu | 87108-87207 | 1 |
| huCTLA-4SA2ex | CAATGCACGTGGCCCAGC CTGCTGTGGTACTGGCCA GCAGCCGAGGCATCGCCA GCTTTG | hu | 87148-87207 | 2 |

TABLE 1-continued

Exemplary CTLA-4 Target Sequences

| Oligomer Target | Sequence (5' to 3') | Sp. | Net. Range | SEQ ID NO. |
|---|---|---|---|---|
| huCTLA-4SA2in | GCATGAGTTCACTGAGTT CCCTTTGGCTTTTCCATG CTAG | nu | 87108-87147 | 3 |
| huCTLA-4SA2sj' | CTTTGGCTTTTCCATGCT AG/CAATGCACGTGGCCC AGCCTGC | hu | 87127-87169 | 22 |
| muCTLA-4SA2sj | TCATGAGCCCACTAAGTG CCCTTTGGACTTTCCATG TCAG/CCATACAGGTGAC CCAACCTTCAGTGGTGTT GGCTAGCAGCCATGGTGT CGCCAGCTTTC | mu | 4262-4361 | 8 |
| muCTLA-4SA2ex | /CCATACAGGTGACCCAA CCTTCAGTGGTGTTGGCT AGCAGCCATGGTGTCGCC AGCTTTC | mu | 4302-4361 | 9 |
| muCTLA-4SA2in | TCATGAGCCCACTAAGTG CCCTTTGGACTTTCCATG TCAG/ | mu | 4262-4301 | 10 |

TABLE 2

ExemplaRy CTLA-4 Targeting Sequences

| Oligamer Target | Sequence (5' to 3') | Sp. | SEQ ID NO. |
|---|---|---|---|
| huCTLA-4SA2ex | GCA GGC TGG GCC ACG TGC ATT G | hu | 4 |
| huCTLA-4SA2sj | CAC GTG CAT TGC TAG CAT GG | hu | 5 |
| huCTLA-4SA2in | CTA GCA TGG AAA AGC CAA AG | hu | 6 |
| huCTLA-4SA2bp | GGA ACT CAG TGA ACT CAT GC | hu | 7 |
| muCTLA-4SA2ex | GGT TGG GTC ACC TGT ATG G | mu | 11 |
| muCTLA4-SA2in | CAT GGA AAG TCC AAA GGG C | mu | 23 |
| muCTLA-4SA3 | CCG GGC ATG GTT CTG GAT C | mu | 12 |
| muCTLA-4SD2 | GTA AGG CGG TGG GTA CAT G | mu | 13 |
| muCTLA-4SD3 | CAT CTT GCT CAA AGA AAC AG | mu | 14 |

B. Treatment Methods

In one aspect, the invention is directed to methods of inducing immunological tolerance in vivo in a patient, by administering to the patient a therapeutically effective amount of a peptide-conjugated CTLA-4 PMO pharmaceutical composition, as described herein, e.g., a pharmaceutical composition comprising an antisense oligomer complementary to a region of SEQ ID NO: 1, e.g., the region of SEQ ID NO: 1 targeted by SEQ ID NOS: 4-6.

In one embodiment, a subject is in need of tolerized T cells when responding to an allogeneic transplantation. In this embodiment, a CTLA-4 antisense compound is administered to the subject in a manner effective to result in blocking the formation of activated T cells. Typically, the patient is treated with the conjugate shortly before, e.g., a few days before, receiving the transplant, then treated periodically, e.g., once every 14 days, until immunological tolerance is established. Immunological tolerance can be monitored during treatment by testing patient T cells for reactivity with donor MHC antigens in a standard in vitro test, as detailed below.

For the treatment of an autoimmune disorder, such as multiple sclerosis, lupis, myathenia gravis, inflammatory bowel disease, rheumatoid arthritis, and Type 1 diabetes (see Example 3), the patient is given an initial single dose of the CTLA-4 antisense conjugate, then additional doses on a periodic basis, e.g., every 1-14 days, until improvement in the disorder is observed. As above, development of immunological tolerance can be monitored during treatment by testing T cells from a blood sample for their ability to react with a selected, relevant antigen in vitro. Alternatively, the ability to treat or prevent the disease condition can be monitored by testing for the status of the condition itself, e.g., measuring blood glucose as a monitor of the state of progression to Type-1 diabetes, as in Example 3. The treatment may be repeated until a desired change in the condition is observed.

It will be understood that in vivo administration of such a CTLA4 antisense compound is dependent upon, (1) the duration, dose and frequency of antisense administration, and (2) the general condition of the subject. A suitable dose can be approximated from animal model studies and extrapolated to patient weight.

Typically, one or more doses of CTLA-4 antisense oligomer are administered, generally at regular intervals for a period of about one to two weeks. Preferred doses for oral administration are from about 5 mg oligomer/patient to about 250 mg oligomer/patient (based on an adult weight of 70 kg). In some cases, doses of greater than 250 mg oligomer/patient may be necessary. For parenteral administration, including intravenous, the preferred doses are from about 5 mg oligomer/patient to about 200 mg oligomer/patient (based on an adult weight of 70 kg).

The antisense agent is generally administered in an amount sufficient to result in a peak blood concentration of at least 200-400 nM antisense oligomer.

In general, the method comprises administering to a subject, in a suitable pharmaceutical carrier, an amount of a CTLA-4 morpholino antisense oligomer effective to alter expression of CTLA-4 mRNA isoforms.

Effective delivery of an antisense oligomer to the target nucleic acid is an important aspect of the methods described herein. In accordance with the invention, such routes of antisense oligomer delivery include, but are not limited to, inhalation; transdermal delivery; various systemic routes, including oral and parenteral routes, e.g., intravenous, subcutaneous, intraperitoneal, or intramuscular delivery.

It is appreciated that any methods which are effective to deliver a CTLA-4 PMO to the cells of an allogeneic transplant or to introduce the agent into the bloodstream are also contemplated.

In preferred applications of the method, the subject is a human subject and the methods of the invention are applicable to treatment of any condition wherein either promoting immunological tolerance or enhancing immune activation would be effective to result in an improved therapeutic outcome for the subject under treatment.

It will be understood that an effective in vivo treatment regimen using a CTLA-4 PMO in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

C. Other Routes of Administration of CTLA-4 Antisense Oligomers

Transdermal delivery of an antisense oligomer may be accomplished by use of a pharmaceutically acceptable carrier. One example of morpholino oligomer delivery is described in PCT patent application WO 97/40854, incorporated herein by reference.

In one preferred embodiment, the oligomer is an anti-CTLA-4 morpholino oligomer, contained in a pharmaceutically acceptable carrier, and delivered orally. In a further aspect of this embodiment, the antisense oligomer is administered at regular intervals for a short time period, e.g., daily for two weeks or less. However, in some cases the antisense oligomer is administered intermittently over a longer period of time.

It follows that a morpholino antisense oligonucleotide composition may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of an antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, an oligonucleotide may be administered in microspheres or microparticles. (See, e.g., Wu et al., 1987).

Sustained release compositions are also contemplated within the scope of this application. These may include semipermeable polymeric matrices in the form of shaped articles such as films or microcapsules.

D. Monitoring Treatment

The efficacy of a given therapeutic regimen involving the methods described herein, may be monitored, e.g., by conventional FACS assays for the phenotype of cells in the circulation of the subject under treatment or cells in culture. Such analysis is useful to monitor changes in the numbers of cells of various lineages, in particular, activated T and B cells in response to an allogeneic transplant.

Phenotypic analysis is generally carried out using monoclonal antibodies specific to the cell type being analyzed. The use of monoclonal antibodies in such phenotypic analyses is routinely employed by those of skill in the art for cellular analyses and monoclonal antibodies specific to particular cell types are commercially available.

The CTLA-4 PMO treatment regimen may be adjusted (dose, frequency, route, etc.), as indicated, based on the results of the phenotypic and biological assays described above.

From the foregoing, it will be appreciated how various objects and features of the invention are met. The specific blockade of activating T cells capable of rejecting transplanted tissues or involved in an autoimmune disorder is an important therapy for numerous human diseases where immunological tolerance is beneficial. The present invention provides a method of specifically blocking the activation of these cells through the use of antisense oligomers designed to inhibit CTLA-4 expression, or enhance expression of specific CTLA-4 isoforms, during the stage of antigen-specific activation and the generation of anergic, tolerized T cells. Antisense CTLA-4 mediated suppression of either chronically activated T cells (i.e. autoimmunity) or naïve T cells responding to alloantigens (transplantation) provides a potent and specific therapeutic effect.

Additionally, this treatment method is long lived because the immune system is unable to replenish antigen-specific T cell clones once the precursor population is removed from the T cell repertoire. In addition, by specifically targeting the antisense CTLA-4 oligomer to activated T cells, naïve T cells would be unaffected, allowing for the patient to respond normally to foreign antigens as soon as the therapy is withdrawn. Moreover, the immune status of the patient prior to the antisense CTLA-4 therapy (e.g. immunity provided by previous vaccinations or infections) would remain intact.

EXAMPLES

The following examples are presented to further illustrate and explain the present invention and should not be taken as limiting in any regard. The examples provide evidence that treatment with a particular CTLA-4 splice altering PMO will enhance the corresponding CTLA-4 mRNA isoform expression in T cells. These effects appear specific, occurring without upregulation of other activation markers.

A model has been established whereby murine splenocytes or purified T cells can be treated with the CTLA-4 slice altering PMOs in vitro. A several-fold increase in CTLA-4 mRNA isoform levels is observed within 24 hours.

An in vivo animal model system using the non-obese diabetic (NOD) mouse has also been used to investigate the ability of the CTLA-4 splice altering PMOs to alter the course of onset of type 1 diabetes (T1D). The NOD mouse is a widely used animal model system for T1D. The compounds of the invention (muCTLA-4SA2; SEQ ID NO:11) are shown to delay onset of T1D in either a prophylactic or therapeutic treatment regimen.

Materials and Methods

Figure 11:
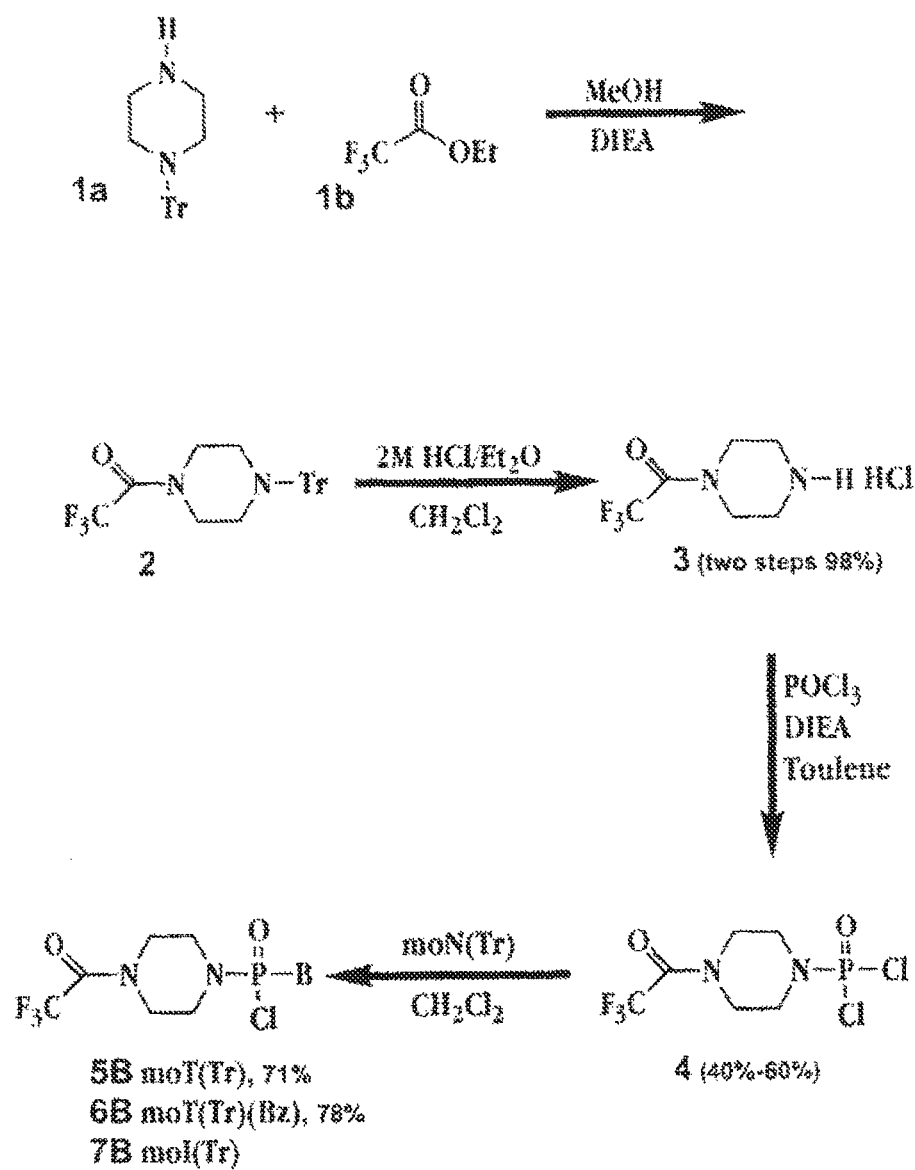
FIG. 11 shows the synthetic steps to produce subunits used to produce +PMO containing the (1-piperazino) phosphinylideneoxy cationic linkage as shown in FIG. 2H.

Phosphorodiamidate morpholino oligomers (PMO) are water-soluble antisense molecules that inhibit or alter gene expression by preventing translation or disrupting mRNA splicing. Murine CTLA-4 antisense PMOs are based on the genomic murine CTLA-4 sequence from GenBank (accession number AF142145) and synthesized by AVI BioPharma's (Corvallis, Oreg.) chemistry group according to previously disclosed methods (Summerton and Weller 1997). A hydrogen is conjugated on the 3' end to each PMO along with the arginine-rich peptide P007-(pip-PDA) (SEQ ID NO:16) on the 5' end. Specific CTLA-4 sequences are as follows: muCTLA-4AUG: 5' CCA AGA CAA GCC ATG GCT GG 3' (SEQ ID NO:31); muCTLA-4SA3: 5' CCG GGC ATG GTT CTG GAT C 3' (SEQ ID NO:12); muCTLA-4SA2ex: 5' GGT TGG GTC ACC TGT ATG G 3' (SEQ ID NO:11); muCTLA-4SA2in: CAT GGA AAG TCC AAA GGG C (SEQ ID NO:23); muCTLA-4SD2: 5' GTA AGG CGG TGG GTA CAT G 3' (SEQ ID NO:13); muCTLA-4SD3: 5' CAT CTT GCT CAA AGA AAC AG 3' (SEQ ID NO:14), Preparation of Morpholino Oligomers Having Cationic Linkages A schematic of a synthetic pathway that can be used to make morpholino subunits containing a (1 piperazino) phosphinylideneoxy linkage is shown in FIG. 11; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

Splenocyte Culturing

Spleens were collected in DME/High Glucose and 1% FBS media. Using a cell strainer (VWR International, West Chester, Pa.) the spleens were sieved into a cell suspension, washed twice, and cultured in Mouse Complete Media (RPMI, 10% FBS, 1% antibiotic, 2% 200 nM L-glutamine, and 50 µM beta-mercapethanol).

Antisense PMO Treatment

Splenocytes from either 86 or NOD mice, at a concentration of 1 to 2 million cells, were plated onto a 12 well plate in Mouse Complete Media. Concanavalin A (Sigma-Aldrich, St. Louis, Mo.) was added at 1 µg/mL per well to induce lymphocyte activation. Lyophilized CTLA-4 PMOs were suspended in sterile PBS and added to specified well cultures. Well plates were incubated at 37° C. for 24 hours.

RNA Extraction

Splenocyte RNA was extracted using Qiagen's RNeasy Mini Kit (Qiagen USA, Valencia, Calif.) as per manufacturer's protocol. All isolated RNA was stored at −80° C.

RT-PCR

To convert isolated RNA to DNA and amplify, Invitrogen's SuperScript™ III One-Step RT-PCR System with Platinum® Taq DNA Polymerase (Invitrogen, Carlsbad, Calif.) was used according to the manufacture's protocol. Targeting the full length CTLA-4 transcript, the following primers were designed from GenBank accession number NM_009843:F 5'-ACA CAT ATG TAG CAC GTA CCT TGG A-3' (SEQ ID NO:32) and R 5'-GGA ATT TTG CAT CCA GCT TTC TAT-3' SEQ ID NO:33). To amplify a portion of the ICOS transcript, the primers F 5'-AAG CCG TAC TTC TGC CGT-3' (SEQ ID NO:34) and R 5'-CCA CAA CGA AAG CTG CAC-3' (SEQ ID NO:35) were designed from GenBank accession number BC034852. Primers targeting the CD28 transcript, F 5'-ATG ACA CTC AGG CTG CTG-3' (SEQ ID NO:36) and R 5'-GCA AGC CAT AAC AAA ACA G-3' SEQ ID NO:37), were designed from GenBank accession number BC034852. All RT-PCR runs were completed on BioRad iCycler iQ Real-Time PCR Detection System (Bio-Rad Laboratories, Hercules, Calif.) according to the following protocol: reverse-transcription reaction at 50° C. for 30 min, DNA polymerase activation at 95° C. for 15 min, 40 cycles of 95° C. denaturation for 30 sec, annealing for 45 sec at 52° C., and extension for 1 min at 72° C., and finally a final extension for 10 min at 72° C. All RT-PCR products were stored at −20° C.

qRT-PCR

The flCTLA-4 and liCTLA-4 quantitative RT-PCR (qRT-PCR) probes and primers were designed by Vijayakrishnan et. al. (Vijayakrishnan, Slavik et al. 2004). The full-length CTLA-4 (flCTLA-4) forward (5' ACT CAT GTA CCC ACC GCC A 3') (SEQ ID NO:38), flCTLA-4 reverse (5' GGG CAT GGT TCT GGA TCA 3') (SEQ ID NO:39) and flCTLA-4 probe (5' CAT GGG CAA CGG GAC GCA GAT TTA T 3') (SEQ ID NO:40) oligonucleotides are as shown. The ligand independent CTLA-4 (liCTLA-4) forward (5' GCC TTT TGT AGC CCT GCT CA 3') (SEQ ID NO:41), liCTLA-4 reverse (5' TCA GAA TCC GGG CAT GGT T 3')(SEQ ID NO:42) and liCTLA-4 probe (5' TTC TTT TCA TCC CAG TCT TCT CTG AAG ATC CA 3')(SEQ ID NO:43) primers are also as shown. The PCR protocol was 10 min at 50° C., 5 min 95° C. and 45 cycles of 95° C. for 10 sec, 58° C. for 30 sec, and 72° C. for 45 sec.

Example 1A

Figure 4A:
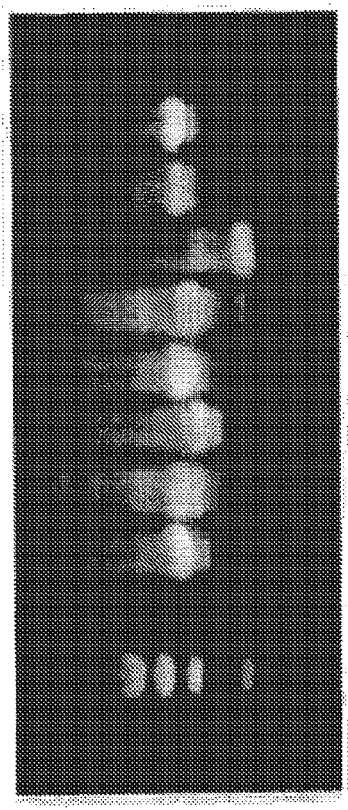
FIGS. 4A-4C show alterations produced in CTLA-4 mRNA derived from B6 and NOD splenocytes after treatment with PMOs targeting splice donor or splice acceptor sequences.
Figure 4B:
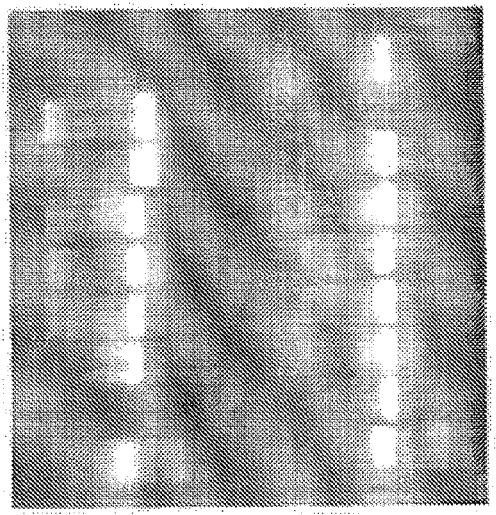
Figure 4C:
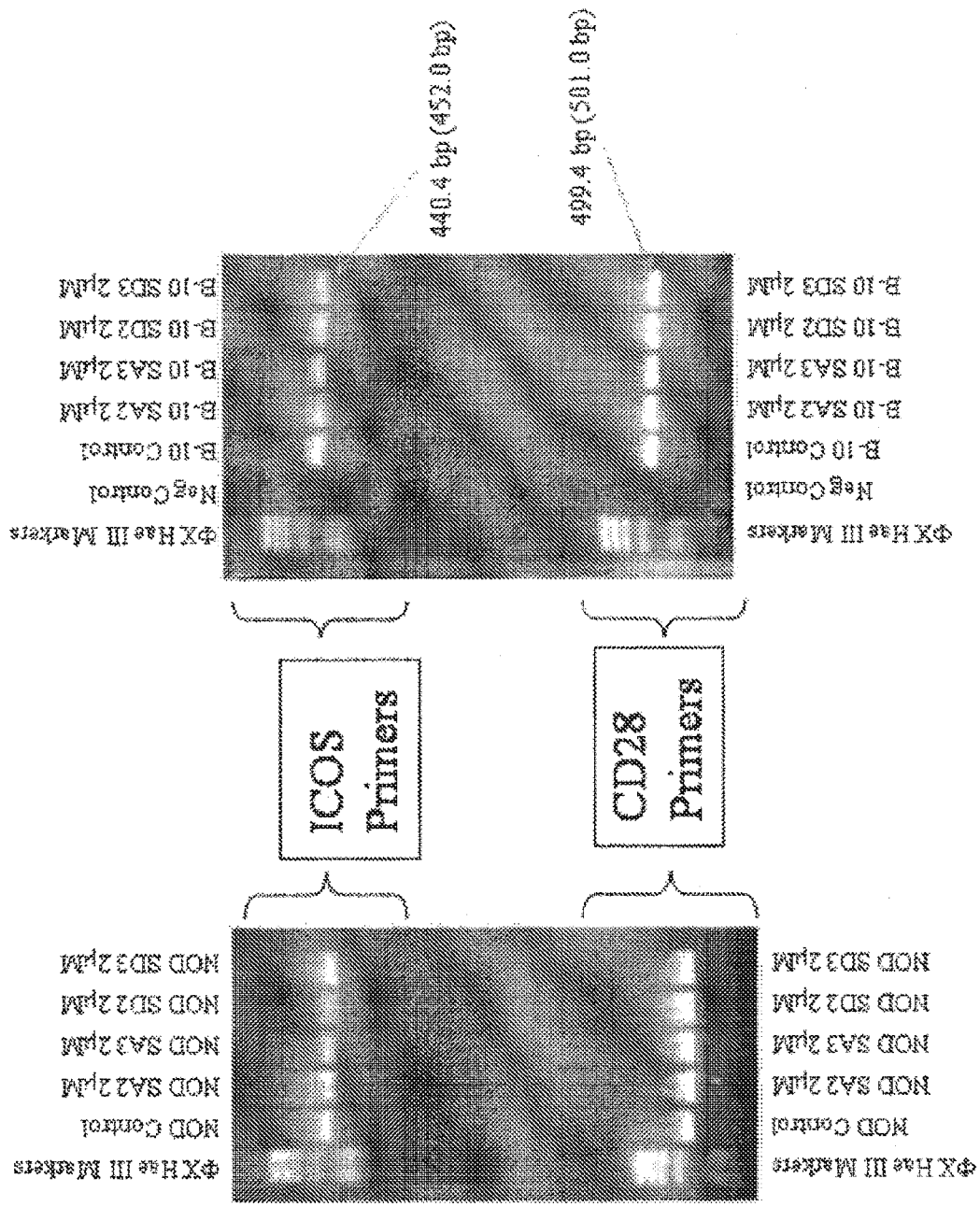

Splice-Altered mRNAs Derived from B6 and NOD Splenocytes after Treatment with PMOs Targeting Splice Donor or Splice Acceptor Sequences CTLA-4 mRNA isoforms were examined by RT-PCR using messenger RNA (mRNA) isolated from B6 splenocytes stimulated with mitogen and treated with the various PMOs (10 micromolar) in culture for 24 hours. Alterations to the size of the products were observed by agarose gel electrophoresis stained with EtBr and are shown in FIG. 4A. PMOs targeting splice acceptor sites (SA) were more efficient for altering splicing compared to those targeting splice donor sites (SD). FIG. 48 shows the results of RT-PCR examination of mRNA derived from NOD splenocytes treated with PMOs. A similar splice alteration pattern as was seen for PMO-treated B6 splenocytes is induced in cells treated with as little as 0.5 micromolar PMO targeting SA2 (muCTLA-4SA2; SEQ ID NO:11). FIG. 4C is a control experiment and shows that protein molecules related to CTLA-4 (ICOS and CD28) Put lacking target homology are unaffected by treatment with CTLA-4 splice altering PMOs. Splenocytes derived from B81 and NOD mice were treated with PMOs and mRNA splice patterns for CD28 and ICOS, molecules related to CTLA-4, were examined by RT-PCR. No alterations to the mRNAs encoding these molecules were detected.

Figure 5:
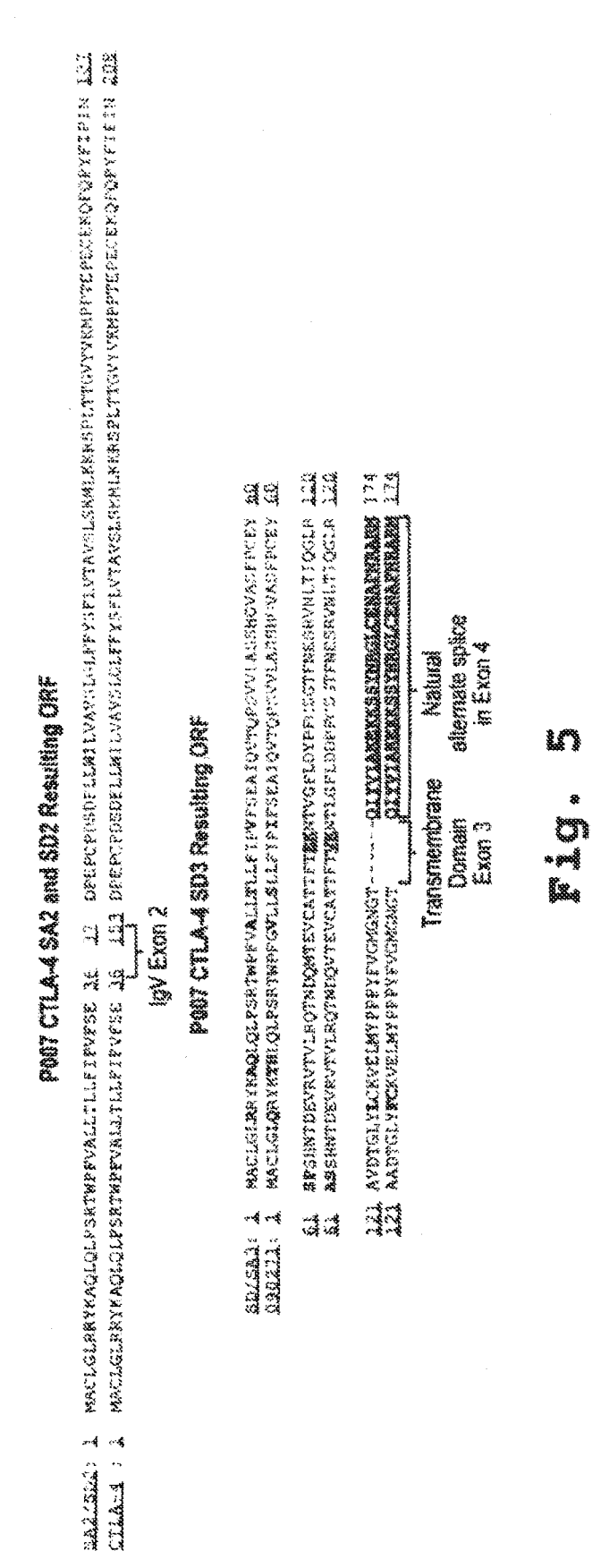

An examination of the alterations made to the CTLA-4 mRNA sequence after treatment with splice altering PMOs was performed to determine if the expected CTLA-4 open reading frames was maintained. The PCR amplicons shown in FIG. 4A were gel isolated, cloned and sequenced to determine the integrity of the polypeptide open reading frame (ORF). The predicted sequence (shown in FIG. 5) as a result of antisense induced excision of exon 2 was obtained with the splice acceptor exon 2 targeting PMO (muCTLA-4SA2; SEQ ID NO:11). Although some of the clones sequenced from cells treated with the exon 3 targeting PMOs were as predicted the dominant sequence was similar to a natural occurring splice form of CTLA-4 form found in rats (GenBank accession number U90271).

Example 1B

Splice-Site Region, Dose, and Specificity Effects

Targeting of sequences surrounding the intron/exon boundary was conducted, employing PPMOs flanking both sides of the SA2 intron-exon boundary as well sequences inside the intron and axon (FIG. 12A). As seen in FIG. 12C, sequences positioned both at the exon side of the SA2 intron/exon boundary (lane 5, SEQ ID NO: 11) and at the intron side of the SA2 intron/exon boundary (lane 4, SEQ ID NO: 23) were effective in inducing liCTLA-4. In addition, a PPMO oligomer sequence positioned 67 bp into the exon (lane 8) was also potent in inducing the altered splice form of the CTLA-4 mRNA.

Figure 13A:
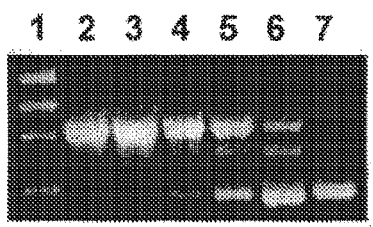
FIGS. 13A and 13B show dose effects and target specificity of induced axon skipping in vitro.

The activity of the SA2 PPMO (SEQ ID NO: 11) was examined to determine if induction of liCTLA-4 behaves in a dose dependent manner, with the results shown in FIG. 13A. In this figure, the lanes represent: (lane 1) φX-Hae III, (lane 2) Control, No Treatment, (lane 3) 0.1 µm, (lane 4) 0.5 µm, (lane 5) 1 µm, (lane 6) 2 µm, and lane (7) 5 µm SA2 oligomer. As seen in the figure, splicing was observed in cells treated with as little as 0.1 µM with about 10-20% altered product and at concentration between 2-5 µM with ~100% altered product.

Figure 13B:
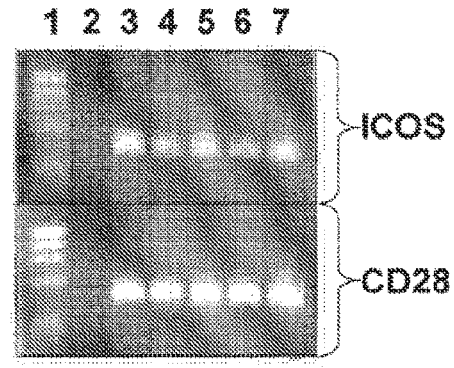

Splicing profiles of other costimulatory molecules related to CTLA-4 were examined to determine if they were affected by treatment with CTLA-4 PPMO. RNA was isolated from cultured NOD splenocytes after treatment with PPMO and examined by RT-PCR using primer pairs specific for CD28 or ICOS to determine if the splice patterns of these mRNA remained normal (FIG. 3b). No alterations to these molecules were detected for either ICOS or CD28, at any of the increasing concentration of SA2 oligomer, as seen in FIG. 13B.

Example 2

Figure 6:
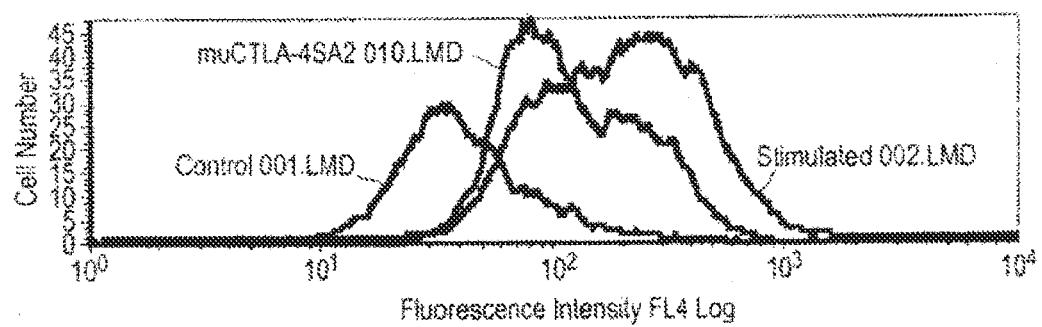
FIG. 6 shows the expression of CD69, an early activation marker, on mouse T cells after treatment with the muCTLA-4SA2 splice altering PMO.

The Effect of CTLA-4 Splice Altering PMOs on T Cell Activation, Proliferation and Adhesion Activity The early activation T cell marker CD69 was examined by flow cytometry after 16 hr treatment with anti-CD3 antibody and with or without treatment with muCTLA-4SA2 PMO (SEQ ID NO:11) at a 5 micromolar concentration. The resulting diminution in CD69 expression compared to untreated stimulated cells demonstrates an influence of the PMO on the activation state of the T cells. The graph in FIG. 6 shows CD69 levels gated on CD4 + cells.

Figure 7:
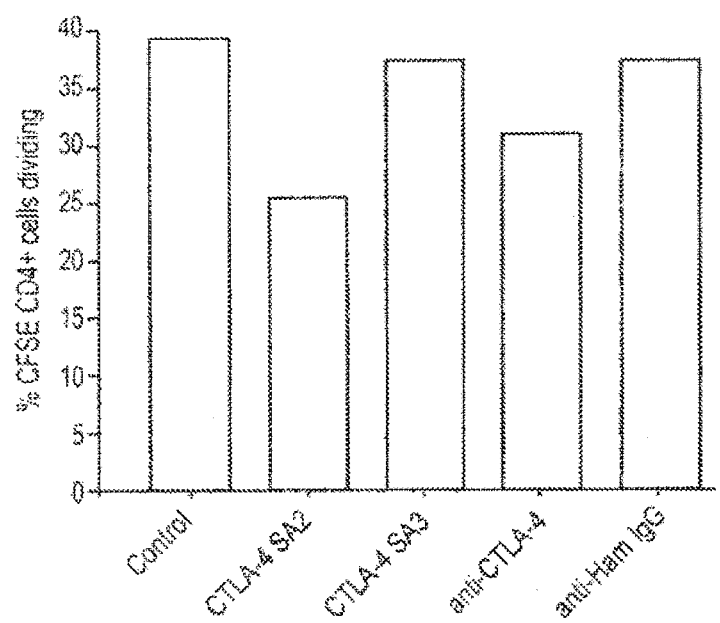
FIG. 7 shows the influence of CTLA-4 splice altering PMOs on T cell proliferation.

The influence of splice altering CTLA-4 PMOs on cell proliferation is shown in FIG. 7. Purified mouse T cells were labeled with CFSE and then stimulated with anti-CD3 antibody. The cells were cultured for 48 hrs with either PMO (5 micromolar) or anti-CTLA-4 antibody or isotype. Cellular division was examined by flow cytometry gating on live cells. Proliferation was inhibited by the CTLA-4 agonist antibody and by treatment with the muCTLA-4SA2 PMO compared to controls as shown in FIG. 7.

Figure 8:
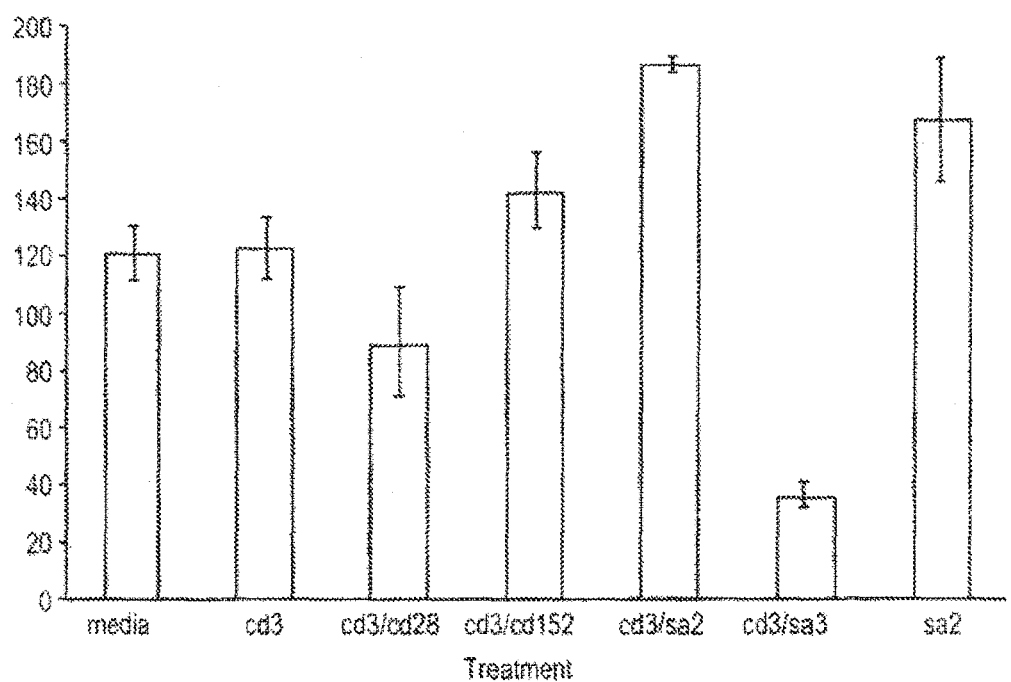
FIG. 8 shows that splice alterations induced by CTLA-4 splice altering PMOs affect the adhesion activity of T cells.

The effect of splice alterations in CTLA-4 on the adhesion activity of T cells is shown in FIG. 8. Costimulation through CTLA-4 has been reported to enhance the adhesion quality of T cells via the capping LFA-1 and subsequent binding to ICAM-1. The EL4 T cell line was used to examine the effect of CTLA-4 splice altering PMOs on T cell adhesion to ICAM-1. Cells were pretreated with PMO (5 micromolar) for 16 hrs or not and then plated onto triplicate wells of a 96 well plate pre-coated with ICAM-1 (12.5 microgram/ml). Cells were then stimulated with anti-CD3 with or without CD28 or CTLA-4 (CD152) (both at 10 microgram/ml) costimulation for 1 hr. The loose cells were removed by inverting the plate. The remaining cells were enumerated using a hemocytometer.

Example 3A

In Vivo Influence of Splice Alteration in CTLA-4 on Diabetes in the NOD Mouse

Figure 14:
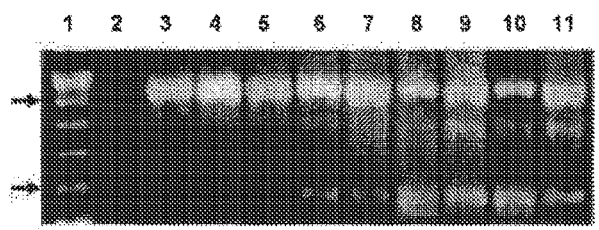
FIG. 14 show in vivo detection of liCTLA-4 induced by treatment with SA2 oligomer and SA2 oligomer plus α-CD3.

An assessment of the splice altering capability of the SA2 PPMO was carried out to determine if in vivo administration would induce the liCTLA-4 form. Female NOD mice (n=6/group) were injected via intraperitoneal (i.p.) route with SA2 (PPMO, SEQ ID NO:11) or saline control once a day for 10 days. On day 10, 3 mice from each of the treatment groups were injected via intravenous (i.v.) route of administration with α-CD3 antibody. Four hours after antibody treatment the pancreatic lymph node was harvested from each animal and processed for isolation of total mRNA. RT-PCR analysis was used to confirm if antisense treatment resulted in an increased expression of liCTLA-4. The resulting cDNAs were examined by agarose gel electrophoresis to determine if a band of the predicted size of liCTLA-4 was observable. All animals receiving the SA2 treatments with or without the addition of α-CD3 exhibited cDNA bands of the approximate predicted size for both flCTLA-4 and liCTLA-4, while no observable liCTLA-4 band was present in any of the saline treated animals. Both upper and lower bands were later verified by sequencing to be the CTLA-4 splice forms (data not shown). Using the same samples, analysis by Real time RT-PCR with a FAM probe specific for the liCTLA-4 was performed to measure level of expression for the various treatment groups (FIG. 14), where the lanes represent: Lane: 1) 100 bp ladder, lane 2) blank, lanes 3-5, saline treated animals, lanes 6-8, SA2 treated animals, and lanes 9-11, SA2+α-CD3 treated animals. As seen, treatment with PPMO alone produced a marked increase in expression of liCTLA-4 over the saline treatment. Additionally there was a significant increase in liCTLA-4 expression (p=0.01 ANOVA) in animals receiving α-CD3 in combination with the PPMO. It was verified that the α-CD3 treatment alone does not induce liCTLA-4 expression in NOD mice by RT-PCR (data not shown), thus confirming that PPMO is responsible for in vivo expression of the isoform.

Example 3B

Treatment of NOD Mice with CTLA-4 PMOs

Figure 9:
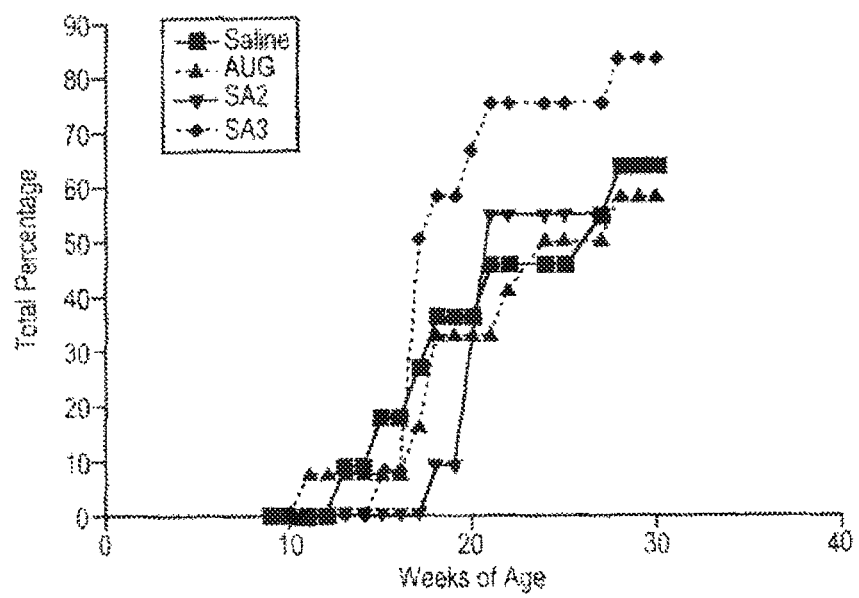
FIG. 9 shows the impact on the onset of diabetes, as measured by elevated blood sugar, after treatment of NOD mice with CTLA-4 splice-altering PMOs.

To examine the in vivo effect of the CTLA-4 splice altering PPMOs, NOD female mice were treated with splice altering PPMOs muCTLA-4SA2 or muCTLA-4SA3 (SEQ ID NOs: 11 and 12, respectively) or a PPMO targeting translation of the CTLA-4 protein AUG (see Materials and Methods). Animals (n=12/group) were treated with PPMO (150 microgram i.p.) in 200 microliter saline for 2 weeks starting at age 8 weeks and blood sugar levels (b.s.l.) monitored weekly. Animals exhibiting a b.s.l. above 250 were terminated. As shown in FIG. 9, animals treated with muCTLA-4SA2 developed disease at a point ~2 weeks later than controls. A greater percentage of animals developed disease when treated with the muCTLA-4SA3 PMO.

Figure 10A:
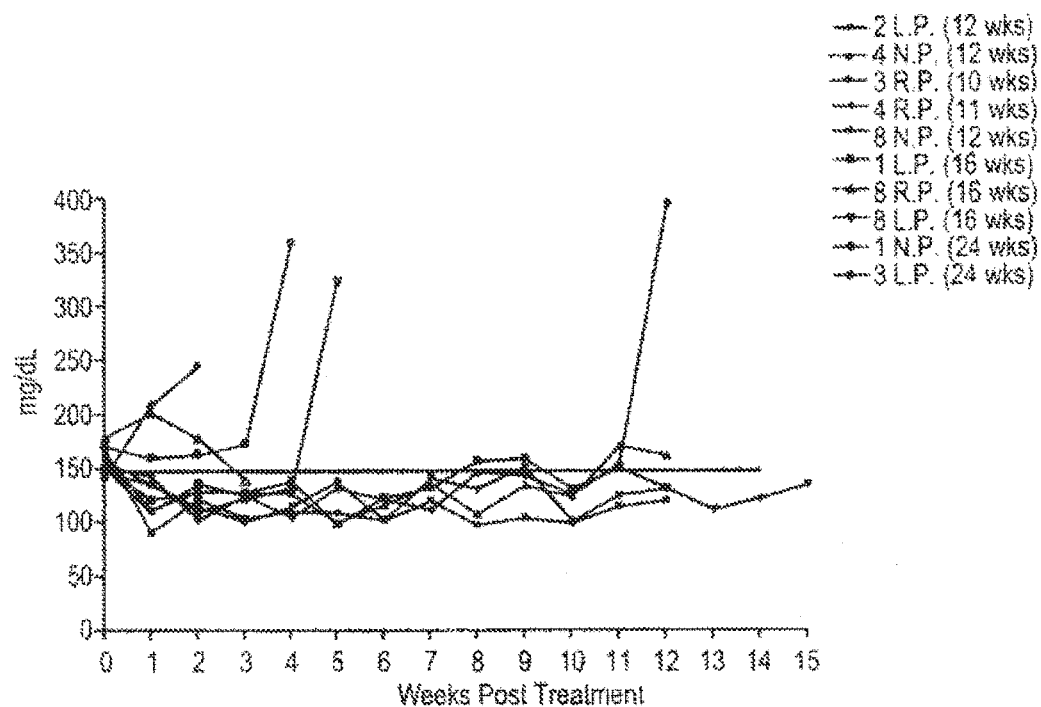
FIGS. 10A and 10B show the impact on the development of elevated blood sugar levels after therapeutic treatment of NOD mice with the muCTLA-4SA2 PMO.

To examine the effect of a therapeutic treatment of NOD mice with the muCTLA-4SA2 PMO, a series of animals were monitored weekly for b.s.l. Treatment with muCTLA-4SA2 PMO (200 micrograms/day i.p. for 14 days) began when b.s.l. exceeded 140 mg/dl regardless of the age on the animal. b.s.l. was monitored until the animal reached at least 24 weeks of age or b.s.l. exceeded 250 mg/dl at which time the animal was euthanized. FIG. 10A shows the results for animals beginning treatment with a b.s.l. below 180 mg/dl.

Figure 10B:
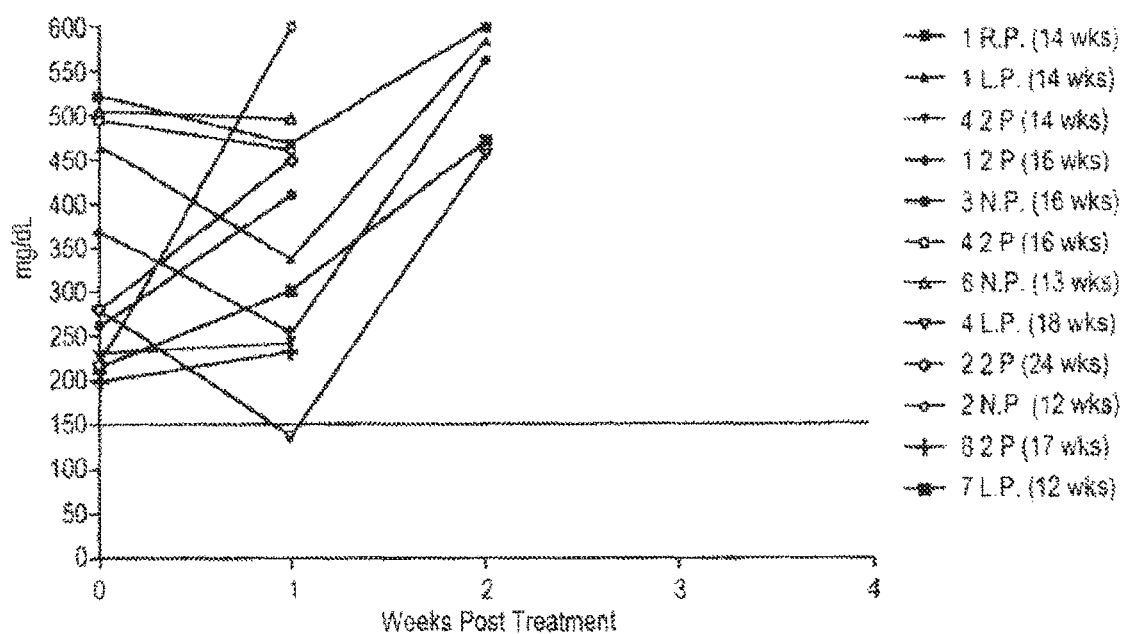

90% of the mice responded to the therapy by exhibiting a decrease in b.s.l. 50% exhibited a prolonged (24 weeks of age or greater) maintenance of normal b.s.l. FIG. 10B shows the results for animals beginning treatment with a b.s.l. above 180 mg/dl. 50 percent of the animals demonstrated a reduction in b.s.l. with one animal transiently returning to near normal levels.

SEQUENCE LISTING

| Name | Target Sequences (5' to 3') | SEQ ID NO |
|---|---|---|
| huCTLA-4SA2sj | GCATGAGTTCACTGAGTTCC CCTTTGGCTTTTCCATGCT AGCAATGCACGTGGCCCAG CCTGCTGTGGTACTGGCCA GCAGCCGAGGCATCGCCAG CTTTG | 1 |
| huCTLA-4SA2ex | CAATGCACGTGGCCCAGCCT GCTGTGGTACTGGCCAGCAG CCGAGGCATCGCCAGCTTTG | 2 |
| huCTLA-4SA2in | GCATGAGTTCACTGAGTTCC CTTTGGCTTTTCCATGCTAG | 3 |
| huCTLA-4SA2sj' | CTTTGGCTTTTCCATGCTAG CAATGCACGTGGCCCAGCCT GC | 22 |
| muCTLA-4SA2sj | TCATGAGCCCACTAAGTGCC CTTTGGACTTTCCATGTCAG CCATACAGGTGACCCAACCT TCAGTGGTGTTGGCTAGCAG CCATGGTGTCGCCAGCTTTC | 8 |
| muCTLA-4SA2ex | CCATACAGGTGACCCAACCT TCAGTGGTGTTGGCTAGCAG CCATGGTGTCGCCAGCTTTC | 9 |
| muCTLA-4SA2in | TCATGAGCCCACTAAGTGCC CTTTGGACTTTCCATGTCAG | 10 |

SEQUENCE LISTING -continued

| Name | Target Sequences (5' to 3') | SEQ ID NO |
|---|---|---|
| Oligomer Targeting Sequences (5' to 3') | | |
| huCTLA-4SA2ex | GCA GGC TGG GCC ACG TGC ATT G | 4 |
| huCTLA-4SA2sj | CAC GTG CAT TGC TAG CAT GG | 5 |
| huCTLA-4SA2bp | CTA GCA TGG AAA AGC CAA AG | 6 |
| huCTLA-4SA2in | GGA ACT CAG TGA ACT CAT GC | 7 |
| muCTLA-4SA2ex | GGT TGG GTC ACC TGT ATG G | 11 |
| muCTLA4-SA2in | CAT GGA AAG TCC AAA GGG C | 23 |
| muCTLA-4SA3 | CCG GGC ATG GTT CTG GAT C | 12 |
| muCTLA-4SD2 | GTA AGG CGG TGG GTA CAT G | 13 |
| muCTLA-4SD3 | CAT CTT GCT CAA AGA AAC AG | 14 |
| Peptide Sequences* | | |
| P003 | $R_9F_2C$ | 15 |
| P007 | $(RAhxR)_4Ahx\beta Ala$ | 16 |
| P008 | $(RAhx)_8\beta Ala$ | 17 |
| RX4 | $(RAhx)_4\beta Ala$ | 18 |
| RXR2 | $(RAhxR)_2Ahx\beta Ala$ | 19 |
| RB8 | $(R\beta Ala)_8$ | 20 |
| CP06062 | $(RAhxRR\beta AlaR)_2Ahx\beta Ala$ | 21 |

*Standard one letter amino acid code used except for 6-aminohexanoic acid (Ahx) and beta-alanine (βAla)

---

It is claimed:

1. A phosphorodiamidate morpholino antisense oligonucleotide of 12 to 40 bases comprising a base sequence that is 100% complementary to contiguous bases of human CTLA-4 pre-mRNA, wherein the base sequence comprises at least 12 contiguous bases that are 100 complementary to SEQ ID NO: 22, and wherein the phosphorodiamidate morpholino antisense oligonucleotide induces skipping of exon 2 of the human CTLA-4 pre-mRNA.

2. The phosphorodiarnidate morpholino antisense oligonucleotide of claim 1, wherein the oligonucleotide is of 15 to 25 bases.

3. The phosphorodiamidate morphohno antisense oligonucleotide of claim 2, wherein the base sequence comprises at least 15 consecutive bases that are 100% complementary to SEQ ID NO: 22.

4. The phosphorodiamidate morpholino antisense oligonucleotide of claim 1, further comprising a polyethylene glycol moiety.

5. The phosphorodiamidate morpholino antisense oligonucleotide of claim 1, wherein the phosphorodiamidate morpholino antisense oligonucleotide comprises phosphorus-containing intersubunit linkages in accordance with the structure:

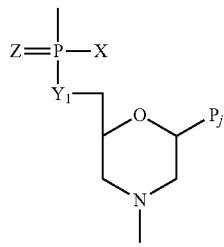

where $Y_1$=O, Z=O, Pj is a purine or pyrimidine base-pairing moiety effective to bind, by base-specific hydrogen bonding, to a base in a polynucleotide, and X is an alkyl amine of form the $NR_2$, where R is independently methyl or H.

6. The phosphorodiamidate morpholino antisense oligonucleotide of claim 5, wherein X is 1-piperazine for at least 2 and no more than half of the total number of phosphorus-containing intersubunit linkages in the phosphorodiamidate morpholino antisense oligonucleotide.

7. The phosphorodiamidate morpholino antisense oligonucleotide of claim 1, wherein the phosphorodiamidate morpholino antisense oligonucleotide is linked to an arginine-rich peptide.

8. A pharmaceutical composition comprising: (a) a phosphorodiamidate morpholino antisense oligonucleotide of 12 to 40 bases comprising a base sequence that is 100% complementary to contiguous bases of human CTLA-4 pre-mRNA, wherein the base sequence comprises at least 12 contiguous bases that are 100% complementary to SEQ ID NO: 22, the region of SEQ ID NO: 1 targeted by the overlapping sequences identified by SEQ ID NOS: 46, and wherein the phosphorodiamidate morpholino antisense oligonucleotide induces skipping of exon 2 of the human CTLA-4 pre-mRNA; and (b) pharmaceutically acceptable carrier.

9. The pharmaceutical composition of claim 8, wherein the phosphorodiamidate morpholino antisense oligonucleotide is of 15 to 25 bases.

10. The pharmaceutical composition of claim 9, wherein the base sequence comprises at least 15 consecutive bases that are 100% complementary to SEQ ID NO 22.

11. The pharmaceutical composition of claim 8, further comprising a polyethylene glycol moiety.

12. The pharmaceutical composition of claim 8, wherein the phosphorodiamidate morpholino antisense oligonucleotide comprises phosphorus-containing intersubunit linkages in accordance with the structure:

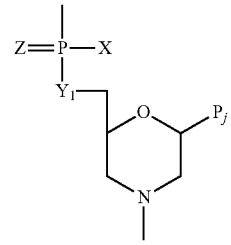

where $Y_1$=O Z=O, Pj is a purine or pyrimidine base-pairing moiety effective to bind, by base-specific hydrogen bonding, to a base in a polynucleotide, and X is an alkyl amine of form the $NR_2$, where R is independently methyl or H.

13. The phosphorodiami date morpholino antisense oligonucleotide of claim 12, wherein X is 1-piperazine for at least 2 and no more than half of the total number of phosphorus-containing intersubunit linkages in the phosphorodianiidate morphohno antisense oligonucleotide.

14. The phosphorodiamidate morpholino antisense oligonucleotide of claim 8, wherein the phosphorodiamidate morpholino antisense oligonucleotide is linked to an arginine-rich peptide.

15. A morpholino antisense oligonucleotide of 12 to 40 bases comprising a base sequence that is 100% complementary to SEQ ID N0: 22, wherein the morpholino antisense oligonucleotide induces skipping of exon 2 of CTLA-4 pre-mRNA.

16. The morpholino antisense oligonucleotide of claim 15, wherein the oligonucleotide is of 15 to 25 bases.

17. The morpholino antisense oligonucleotide of claim 15, wherein the oligonucleotide is of 18 to 25 bases.

18. The morpholino antisense oligonucleotide of claim 15, further comprising a polyethylene glycol moiety.

19. The morpholino antisense oligonucleotide of claim 15, wherein the morpholino antisense oligonucleotide comprises phosphorus-containing intersubunit linkages in accordance with the structure:

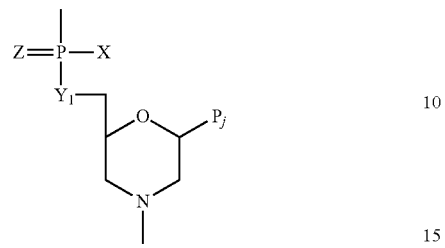

where $Y_1 = O$, $Z = O$, Pj is a purine or pyrimidine base-pairing moiety effective to bind, by base-specific hydrogen bonding, to a base in a polynucleotide, and X is selected from alkyl, alkoxy, thioalkoxy, and alkyl amino.

20. The morpholino antisense oligonucleotide of claim 19, wherein X is 1-piperazine for at least 2 and no more than half of the total number of phosphorus-containing intersubunit linkages in the morpholino antisense oligonucleotide.

21. The morpholino anti sense oligonucleotide of claim 15, wherein the morpholino antisense oligonucleotide is linked to an arginine-rich peptide.

* * * * *

UNITED STATES PATENT AND TRADEMARK OFFICE
CERTIFICATE OF CORRECTION

PATENT NO. : 9,487,786 B2  
APPLICATION NO. : 14/581485  
DATED : November 8, 2016  
INVENTOR(S) : Dan V. Mourich et al.

Page 1 of 2

It is certified that error appears in the above-identified patent and that said Letters Patent is hereby corrected as shown below:

In the Claims

Column 41, Line 20:
"at least 12 contiguous bases that are 100 complementary to" should read, --at least 12 contiguous bases that are 100% complementary to--.

Column 41, Line 24:
"2. The phosphorodiarnidate morpholino antisense" should read, --2. The phosphorodiamidate morpholino antisense--.

Column 41, Line 27:
"3. The phosphorodiamidate morphohno antisense" should read, --3. The phosphorodiamidate morpholino antisense--.

Column 42, Line 16:
"overlapping sequences identified by SEQ ID NOS: 46, and" should read, --overlapping sequences identified by SEQ ID NOS: 4-6, and--.

Column 42, Line 19:
"CTLA-4 pre-mRNA; and (b) pharmaceutically acceptable" should read, --CTLA-4 pre-mRNA; and (b) a pharmaceutically acceptable--.

Column 42, Line 26:
"that are 100% complementary to SEQ ID NO 22" should read, --that are 100% complementary to SEQ ID NO: 22--.

Column 42, Line 48:
"13. The phosphorodiami date morpholino antisense" should read, --13. The phosphorodiamidate morpholino antisense--.

Signed and Sealed this  
Twenty-sixth Day of June, 2018

Andrei Iancu  
*Director of the United States Patent and Trademark Office*

CERTIFICATE OF CORRECTION (continued)
U.S. Pat. No. 9,487,786 B2

Column 42, Lines 52-53:
"phosphorus-containing intersubutnit linkages in the phosphorodianiidate morphohno antisense oligonucleotide" should read, --phosphorus-containing intersubunit linkages in the phosphorodiamidate morpholino antisense oligonucleotide--.

Column 42, Line 59:
"to SEQ ID N0: 22, wherein the morpholino antisense" should read, --to SEQ ID NO: 22 wherein the morpholino antisense--.

Column 43, Line 26:
"21. The morpholino anti sense oligonucleotide of claim" should read, --21. The morpholino antisense oligonucleotide of claim--.